(12) United States Patent
Pantaleo et al.

(10) Patent No.: US 9,146,236 B2
(45) Date of Patent: Sep. 29, 2015

(54) METHODS FOR DIFFERENTIATING BETWEEN DISEASE STATES

(76) Inventors: Giuseppe Pantaleo, Lausanne (CH);
Alexandre Harari, Lausanne (CH);
Matthieu Perreau, Lausanne (CH)

( * ) Notice: Subject to any disclaimer, the term of this patent is extended or adjusted under 35 U.S.C. 154(b) by 87 days.

(21) Appl. No.: 13/996,649

(22) PCT Filed: Dec. 22, 2011

(86) PCT No.: PCT/IB2011/003145
§ 371 (c)(1),
(2), (4) Date: Sep. 5, 2013

(87) PCT Pub. No.: WO2012/085652
PCT Pub. Date: Jun. 28, 2012

(65) Prior Publication Data
US 2013/0338059 A1    Dec. 19, 2013

Related U.S. Application Data

(60) Provisional application No. 61/426,853, filed on Dec. 23, 2010.

(51) Int. Cl.
*G01N 33/50* (2006.01)
*G01N 33/68* (2006.01)
*G01N 33/569* (2006.01)

(52) U.S. Cl.
CPC ........ *G01N 33/5695* (2013.01); *G01N 33/6863* (2013.01); *G01N 2333/35* (2013.01); *G01N 2333/525* (2013.01); *G01N 2333/55* (2013.01); *G01N 2333/57* (2013.01)

(58) Field of Classification Search
None
See application file for complete search history.

(56) References Cited

U.S. PATENT DOCUMENTS

| | | | |
|---|---|---|---|
| 8,765,366 B2 * | 7/2014 | Lalvani et al. | 435/4 |
| 8,975,069 B2 * | 3/2015 | Kelleher et al. | 435/372.3 |
| 2013/0122523 A1 | 5/2013 | Bahlmann et al. | |
| 2013/0338059 A1 * | 12/2013 | Pantaleo et al. | 514/2.9 |
| 2014/0342936 A1 * | 11/2014 | Rubbo et al. | 506/9 |
| 2015/0099652 A1 * | 4/2015 | Bahlmann et al. | 506/9 |

FOREIGN PATENT DOCUMENTS

| | | | |
|---|---|---|---|
| EP | 2655662 A2 * | 10/2013 | |
| WO | WO 2007/107714 A2 * | 9/2007 | |
| WO | PCT/IB2011/003145 | 9/2012 | |
| WO | WO 2012/085652 A3 * | 11/2012 | |
| WO | WO 2014/140833 A2 * | 9/2014 | |

OTHER PUBLICATIONS

Harari et al, Nature Medicine vol. 17 | No. 3 | Mar. 2011 | 372-377.*
Rozot et al, Clinical Infectious Diseases® 2015;60(3):432-7.*
Prezzemolo et al, Frontiers in Immunology | Microbial Immunology Apr. 2014 | vol. 5 | Article 180 | 1-13.*
Bhatt et al. 2015. Quest for correlates of protection against tuberculosis. Clin Vaccine Immunol 22:258-266.*
Hutchinson et al. 2015. Measurement of phenotype and absolute number of circulating heparinbinding hemagglutinin, ESAT-6 and CFP-10, and purified protein derivative antigen-specific CD4 T cells can discriminate active from latent tuberculosis infection. Clin Vaccine Immunol 22:200-212.*
Borgstrom et al. (2012) Immune Responses to ESAT-6 and CFP-10 by FASCIA and Multiplex Technology for Diagnosis of *M. tuberculosis* Infection; IP-10 is a Promising Marker. PLoS ONE 7(11): e43438. 11 pages.*
Sutherland JS, de Jong BC, Jeffries DJ, Adetifa IM, Ota MOC (2010) Production of TNF-a, IL-12(p40) and IL-17 Can Discriminate between Active TB Disease and Latent Infection in a West African Cohort. PLoS ONE 5(8): e12365. 10 pages.*
Hur et al. Journal of Infection (2015) 70, 346-355.*
Kim et al, Scandinavian Journal of Immunology © 2012, 76, 580-586.*
Xia et al, Zhongguo Weishengtaixue Zazhi (2013), 25(3), 306-308, abstract only.*
Berry, M.P., et al. An interferon-inducible neutrophil-driven blood transcriptional signature in human tuberculosis. Nature 466, 973-977 (2010).
Betts, M.R., et al. HIV nonprogressors preferentially maintain highly functional HIV-specific CD8+ T cells. Blood 107, 4781-4789 (2006).
Caccamo, et al. Analysis of *Mycobacterium tuberculosis*-Specific CD8 T-Cells in Patients with Active Tuberculosis and in Individuals with Latent Infection. PLoS ONE 4(5): e5528 (2009).
Day, et al. Detection of polyfunctional *Mycobacterium tuberculosis*-specific T cells and association with viral load in HIV-1-infected persons. J Infect Dis 197, 990-999 (2008).
Ewer, K., et al. Comparison of T-cell-based assay with tuberculin skin test for diagnosis of *Mycobacterium tuberculosis* infection in a school tuberculosis outbreak. Lancet 361, 1168-1173 (2003).
Feldmann, et al. Anti-TNF alpha therapy of rheumatoid arthritis: what have we learned? Annu Rev Immunol 19, 163-196 (2001).
Flynn, et al. Tumor necrosis factor-alpha is required in the protective immune response against *Mycobacterium tuberculosis* in mice. Immunity 2, 561-572 (1995).
Flynn, et al. Immunology of tuberculosis. Annu Rev Immunol 19, 93-129 (2001).
Griner, et al. Selection and interpretation of diagnostic tests and procedures. Principles and applications. Ann Intern Med 94, 557-592 (1981).
Harari, et al. Functional signatures of protective antiviral T-cell immunity in human virus infections. Immunol Rev 211, 236-254 (2006).
Harari, et al. An HIV-1 clade C DNA prime, NYVAC boost vaccine regimen induces reliable, polyfunctional, and long-lasting T cell responses. J Exp Med 205, 63-77 (2008).
Jasmer, et al. Clinical practice. Latent tuberculosis infection. N Engl J Med 347, 1860-1866 (2002).

(Continued)

*Primary Examiner* — Nita M Minnifield
(74) *Attorney, Agent, or Firm* — Patrick J. Halloran

(57) ABSTRACT

This disclosure relates to methods for differentiating between mammals having active and latent Tuberculosis disease, by determining the percentage of polyfunctional CD4+ T-cells expressing TNF-alpha, IFN-gamma, and IL-2, or by determining expression of IL-17.

17 Claims, 20 Drawing Sheets

(56) References Cited

OTHER PUBLICATIONS

Kaufmann, S.H. How can immunology contribute to the control of tuberculosis? Nat Rev Immunol 1, 20-30 (2001).

Lalvani, et al. Enhanced contact tracing and spatial tracking of *Mycobacterium tuberculosis* infection by enumeration of antigen-specific T cells. Lancet 357, 2017-2021 (2001).

Lamoreaux, et al. Intracellular cytokine optimization and standard operating procedure. Nat Protoc 1, 1507-1516 (2006).

Maini, et al. Infliximab (chimeric anti-tumour necrosis factor alpha monoclonal antibody) versus placebo in rheumatoid arthritis patients receiving concomitant methotrexate: a randomised phase III trial. ATTRACT Study Group. Lancet 354, 1932-1939 (1999).

Meier, et al. Sensitivity of a new commercial enzyme-linked immunospot assay (T SPOT-TB) for diagnosis of tuberculosis in clinical practice. Eur J Clin Microbiol Infect Dis 24, 529-536 (2005).

Metz, C.E. Basic principles of ROC analysis. Semin. Nucl. Med. 8, 283-298 (1978).

Pantaleo, et al. Correlates of immune protection in HIV-1 infection: what we know, what we don't know, what we should know. Nat Med 10, 806-810 (2004).

Pantaleo, et al. Functional signatures in antiviral T-cell immunity for monitoring virus-associated diseases. Nat Rev Immunol 6, 417-423 (2006).

Sutherland, et al. Pattern and diversity of cytokine production differentiates between *Mycobacterium tuberculosis* infection and disease. Eur J Immunol 39, 723-729 (2009).

Young, et al. Explaned polyfunctional T cell response to mycobacterial antigens in TB disease and contraction post-treatment. PLOS One, Public Library of Science, 5(6): 11237-1 (2010).

Zimmerli, et al. HIV-1-specific IFN-gamma/IL-2-secreting CD8 T cells support CD4-independent proliferation of HIV-1-specific CD8 T cells. Proc Natl Acad Sci U S A 102, 7239-7244 (2005).

Zweig, et al. Receiver-operating characteristic (ROC) plots: a fundamental evaluation tool in clinical medicine. Clin Chem 39, 561-577 (1993).

* cited by examiner

FIGURE 6

| Patient code # | Gender | Age | Clinical history | PCR | AFS[1] | Culture[3] | Cytology and Histopathology | Diagnosis | Treatment | Comments |
|---|---|---|---|---|---|---|---|---|---|---|
| A1 | F | 31 | Typical clinical presentation (weight loss, malaise, productive coughing and hemoptysis, night sweats) | + | + | + | NA* | Pulmonary TB | Rifampicine, isoniazide, pyrazinamide and ethambutol | PCR, AFS and culture performed on sputum. |
| A2 | F | 59 | End-stage renal disease related to SLE, APLS. Chronic HCV. Weight loss, fever and liver tests abnormality | + | + | - | Bone marrow aspiration and biopsy | Disseminated TB | Rifampicine, ethambutol and amikacine | Positive AFS and PCR in bronchoalveolar lavage (BAL) |
| A3 | M | 27 | Fever, pleural effusion, necrotic lymphadenopathy | + | - | - | Cytology of pleural fluid 95% of small lymphocytes | Disseminated TB | Rifampicine, isoniazide, pyrazinamide and ethambutol | Positive PCR, increase of adenosine deaminase and lymphocytosis in pleural fluid |
| A4 | F | 78 | Fatigue, weight loss, night sweats. Sterile leucocyturia. CT-scan: micronodules in lungs and spleen | + | + | + | Bronchial biopsy showing caseous necrosis with granulomatous inflammation | Disseminated TB | Rifampicine, isoniazide, pyrazinamide and ethambutol | Rheumatoid arthritis previously treated with methotrexate, leflunomide and steroids. Modification of therapy: isoniazide introduced prior to initiation of adalimumab (ELISpot TB +) |
| A5 | F | 35 | After delivery: cough, fever, night sweats, chest and abdominal pain. CT-scan: pleural effusion and tubo-ovarian abscesses | + | + | + | Bilateral granulomatous and necrotic salpingitis with AFS resistant bacilli | Disseminated TB | Rifampicine, isoniazide, pyrazinamide and ethambutol | HIV infection treated with didanosine, lamivudine and lopinavir/ritonavir (CD4 count 152 cells/µL, viremia <40 HIV-1 RNA copies/mL). PCR, AFS and culture positive in peritoneal samples. Increase of adenosine deaminase in pleural fluid |
| A6 | M | 8 | Immigration routine chest X-ray: pulmonary caverna | + | + | + | Granulomatous and necrotic inflammation and calcifications on the lobectomy histopathology | Pulmonary TB | Rifampicine, isoniazide, pyrazinamide and ethambutol | Positive AFS, culture and PCR in sputum, not on the lobectomy tissue. Negative PPD test. |
| A7 | M | 15 | Fever, fatigue, asthenia, loss of weight, night sweats, and chest pain. Left hilar and retroperitoneal lymphadenopathies on thoraco-abdominal CT-scan | - | - | - | NA | Lymph nodes TB | Rifampicine, isoniazide and pyrazinamide | PPD skin test positive. Complete remission after TB treatment |
| A8 | F | 49 | Fever, weight loss, chills, productive cough. Chest X-ray: bilateral pneumonia. Chest CT-scan: right upper and middle lobes hepatisation | + | + | + | NA | Pulmonary TB | Rifampicine, isoniazide, pyrazinamide, ethambutol, moxifloxacine | HIV infection treated with tenofovir, emtricitabine and efavirenz (CD4 count 285 cells/µL, viremia <40 HIV-1 RNA copies/mL). PCR, AFS and culture performed on sputum |
| A9 | F | 72 | Cough, severe loss of weight. Confusion. Numerous bilateral lung nodules on chest X-ray and CT-scan | + | + | + | AFS positive bacilli on the bronchoalveolar lavage (BAL) cytology | Pulmonary TB | Rifampicine, isoniazide, pyrazinamide and ethambutol | AFS, culture and PCR positive in bronchoalveolar lavage (BAL). Probable reactivation of latent TB |
| A10 | M | 52 | Fever, asthenia, chills, large cervical adenopathy. Hepatosplenomegaly on the abdominal CT-scan | + | - | + | Lymph node cytoponction: positive staining and PCR. Epithelioid granulomas on the bone marrow and liver biopsies | Disseminated TB | Rifampicine, isoniazide, pyrazinamide and ethambutol | Recent diagnosis of HIV infection (no treatment): CD4 count 18 cells/µL, viremia 207'000 HIV-1 RNA copies/mL. Chronic HCV infection (genotype 3a) |
| A11 | M | 40 | Cough, night sweats, severe weight loss. Pulmonary infiltrates and caverna on the chest X-ray | + | + | + | NA | Pulmonary TB | Rifampicine, isoniazide, pyrazinamide and ethambutol | Positive AFS, culture and PCR in sputum |

AFS (acid-fast staining) and culture performed according to Murray et al. Manual of Clinical Microbiology, American Society of Microbiology. *Not applicable Analysis of *Mtb-specific* T-cell responses in the patients from the test cohort (n=48) among those screened prior to anti-TNF-α treatment (thereafter referred to as patients from RHU, n=20) and the others (n=28)

FIGURE 11

| Patient code # | Gender | Age | PCR | AFB § | Culture § | Diagnosis |
|---|---|---|---|---|---|---|
| CH-1 | F | 63 | - | - | - | Disseminated TB |
| CH-2 | F | 30 | + | - | + | Lymph Node TB |
| CH-3 | M | 76 | + | + | + | Disseminated TB |
| CH-4 | M | 30 | - | - | + | Pulmonary TB |
| CH-5 | M | 54 | + | + | + | Pulmonary TB |
| CH-6 | F | 38 | + | + | + | Disseminated TB |
| RSA-1 | M | 41 | * | + | + | Pulmonary TB |
| RSA-2 | M | 59 | * | - | + | Pulmonary TB |
| RSA-3 | M | 31 | * | + | + | Pulmonary TB |
| RSA-4 | M | 31 | * | - | + | Pulmonary TB |
| RSA-5 | M | 47 | * | - | + | Pulmonary TB |
| RSA-6 | M | 37 | * | + | + | Pulmonary TB |
| RSA-7 | M | 54 | * | - | + | Pulmonary TB |
| RSA-8 | M | 50 | * | + | + | Pulmonary TB |
| RSA-9 | M | 38 | * | - | + | Pulmonary TB |
| RSA-10 | M | 51 | * | - | + | Pulmonary TB |
| RSA-11 | M | 23 | * | + | + | Pulmonary TB |
| RSA-12 | M | 45 | * | - | + | Pulmonary TB |

* Not done
CH: patients from Switzerland; RSA: patients from the Republic of South Africa
§ AFB (acid-fast bacilli) and culture performed according to Murray et al., Manual of Clinical Microbiology, American Society of Microbiology

METHODS FOR DIFFERENTIATING BETWEEN DISEASE STATES

RELATED APPLICATIONS

This application is a 35 U.S.C. 0371 national stage application of International Application No. PCT/IB2011/003145, filed Dec. 22, 2011, and claims priority to U.S. Prov. Appln. No. 61/426,853 filed Dec. 23, 2010, which are incorporated by reference herein in their entirety.

FIELD OF THE DISCLOSURE

This disclosure relates to methods for differentiating between mammals having active and latent Tuberculosis disease.

BACKGROUND OF THE DISCLOSURE

Cellular immunity and particularly CD4 T-cells have a central role in the control of *Mycobacterium tuberculosis* (Mtb) infection IFN-γ and TNF-α are thought to be crucial for protection against Mtb. Diagnosis of Mtb infection remains complex and requires several clinical, radiological, histopathological, bacteriological and molecular parameters. IFN-γ-release assays (IGRAs), i.e. Quantiferon and ELISpot, measure responses to antigens (e.g., ESAT-6 or CFP-10) that are mainly limited to Mtb, and discriminate infection from immunity induced by vaccination with Bacille Calmette-Guérin (BCG). IGRAs however do not discriminate between active disease and latent infection. While IFN-γ production alone showed no correlation with disease activity in chronic virus infection, polyfunctional (IFN-γ+IL-2+TNF-α) profiles of pathogen-specific T-cell responses have been correlated with disease activity. A definite correlation between active and latent Mtb infection, suitable for incorporation into an assay for differentiating between the two conditions, has not yet been described. Previous work has described a rough correlation between active disease and the presence of >50% of Mtb-reactive CD4 T cells producing TNF-α that do not also produce IFN-γ and IL-2 (e.g., TNF-α monospecific cells). However, this rough correlation was not sufficiently accurate or specific to serve as a true diagnostic tool. As described below, a specific correlation has been identified and an accurate, reproducible assay system for differentiating between active and latent infection by Mtb provided.

BRIEF DESCRIPTION OF THE DRAWINGS

FIG. 6. Clinical description of patients diagnosed with active TB disease from the test cohort.

All the possible combinations of the different functions are shown on the x axis whereas the frequencies of Mtb-specific cytokine-producing CD4 T-cells are shown on the y axis. The pie charts summarize the data, and each slice corresponds to the proportion of Mtb-specific CD4 T-cells positive for a certain combination of functions.

Figure 9:
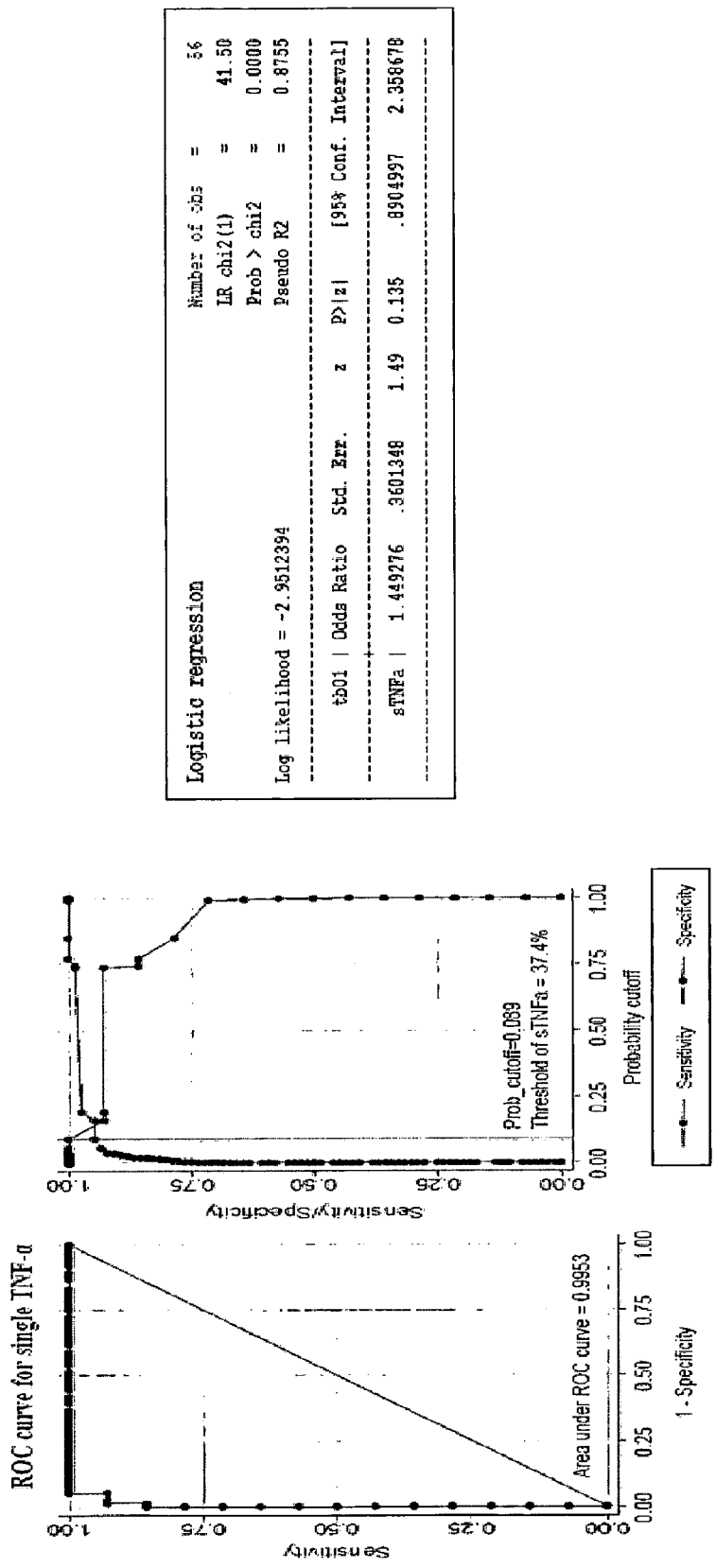

FIG. 9. Logistic regression analysis (left panel) showing the association between the proportion of single TNF-α with the ability to discriminate between active TB disease and latent Mtb infection (AUC=0.995; [95% confidence interval: 0.984-1]; Odds-Ratio=1.45) from the test cohort. Right panel shows that a cutoff of 37.4% (of single TNF-α-producing CD4 T cells) was calculated as the value associated with a sensitivity of 100% and specificity of 96%.

Figure 10:
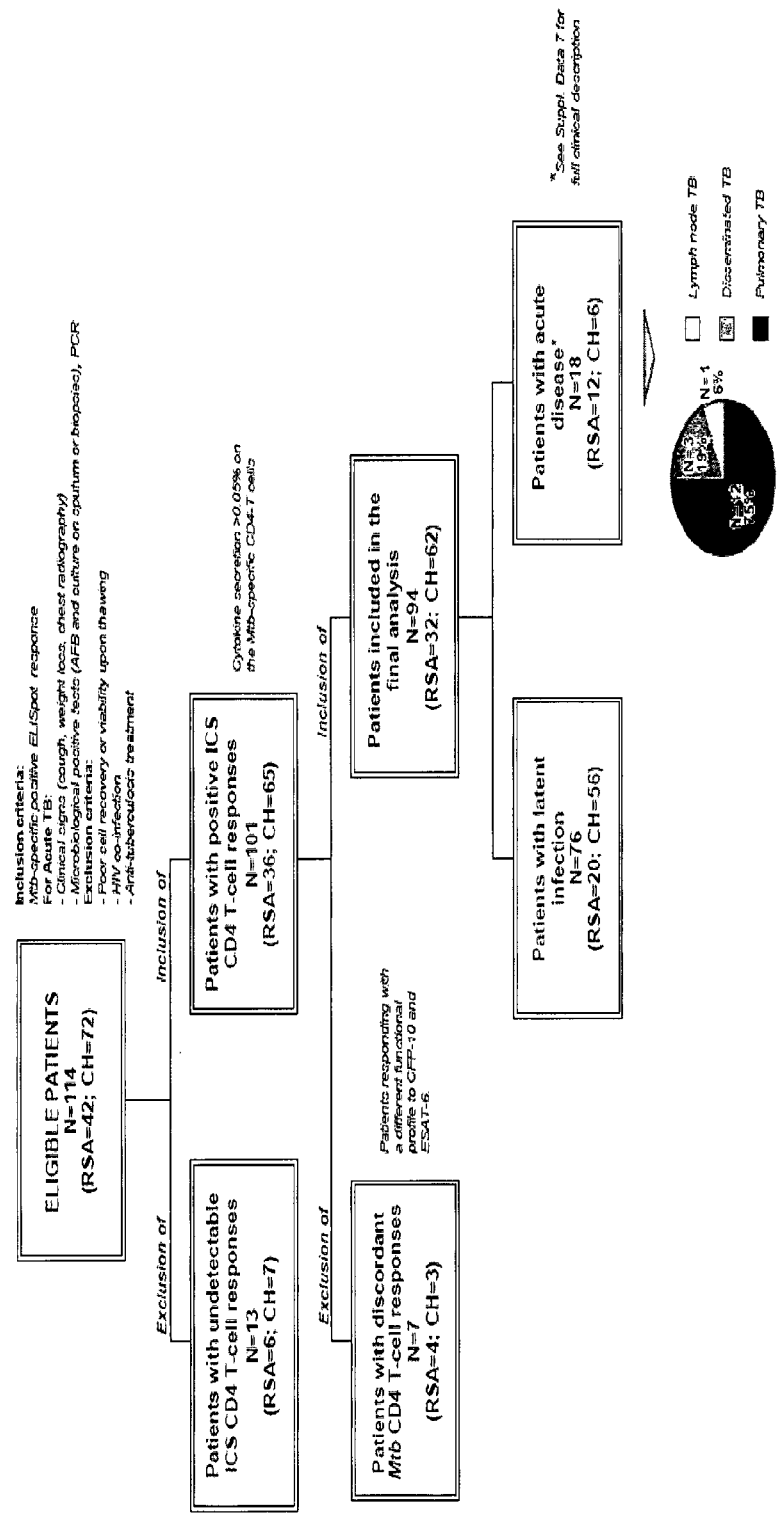

FIG. 10. Flow chart description of patients included in the validation cohort.

FIG. 11. Clinical description of patients diagnosed with active TB disease from the validation cohort.

Figure 12:
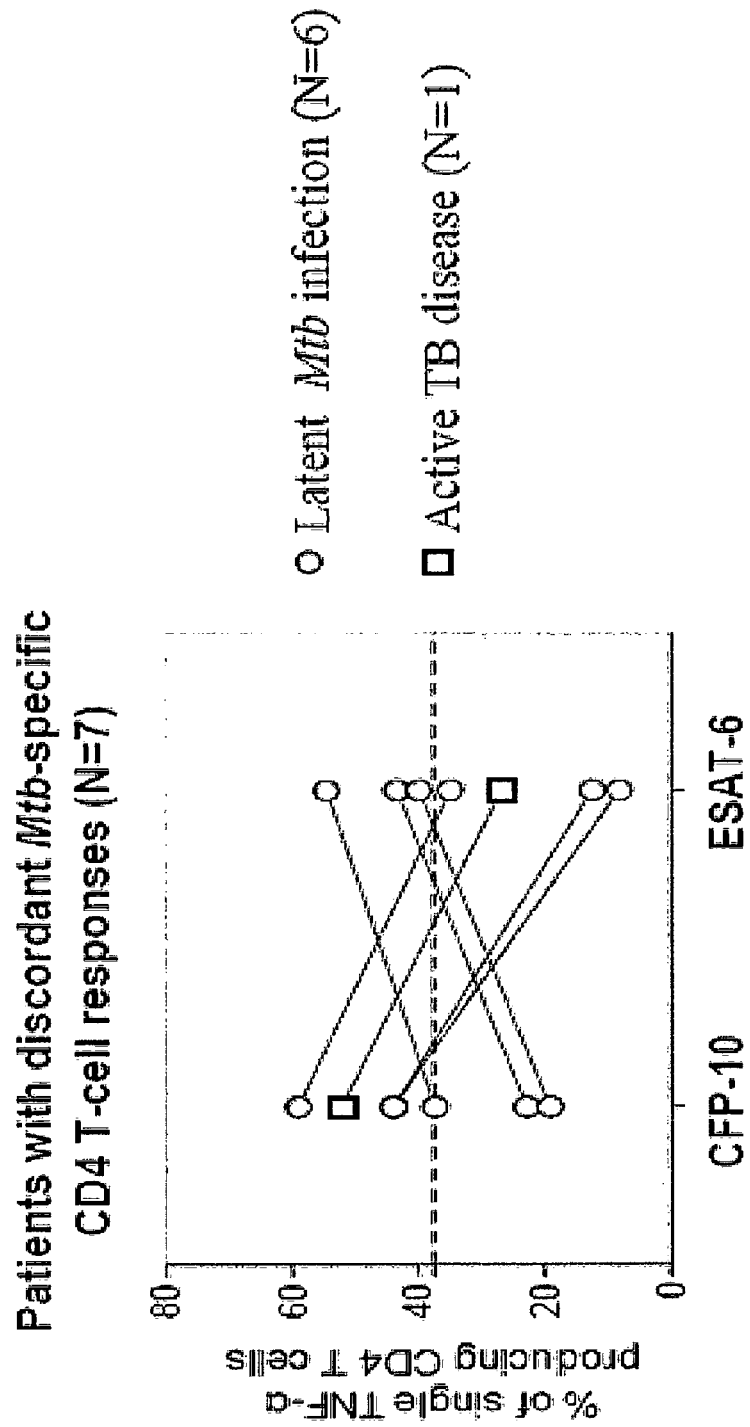

FIG. 12. Percentages of Mtb-specific single TNF-α-producing CD4 T-cells in the 7 participants (among 101) with discordant responses against ESAT-6 and CFP-10 peptide pools. Dashed line represents the cutoff of 37.4% of single TNF-α. Participants with latent Mtb infection (N=6) are represented with red circles whereas the patient with active TB disease (N=1) is shown with blue squares.

Figure 13:
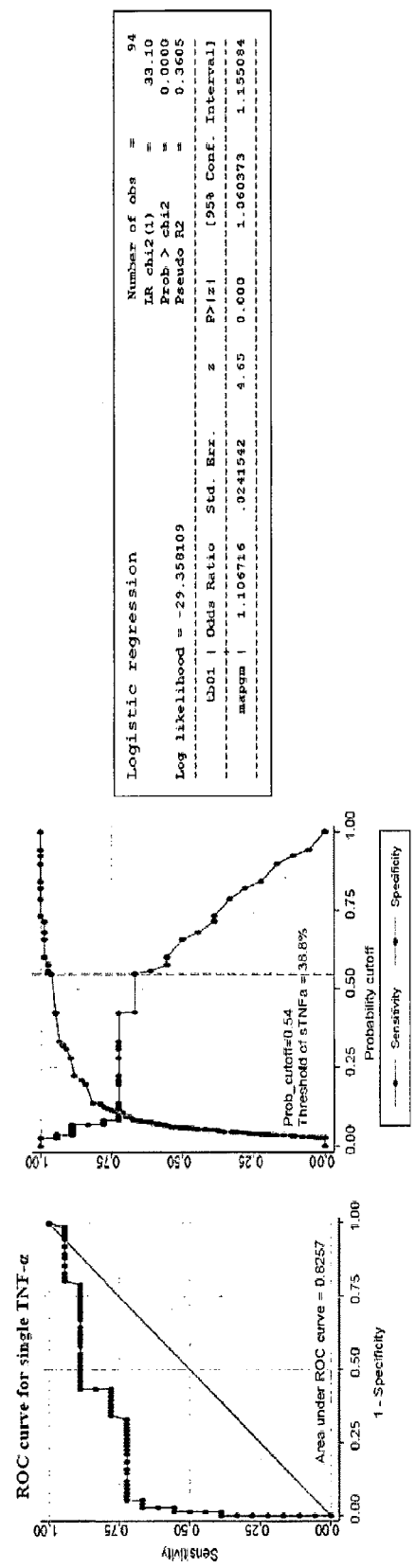

FIG. 13. Overall performance of the test showing positive and negative predictive values, sensitivity and specificity (top panel). Logistic regression analysis (left bottom panel) showing the association between the proportion of single TNF-α with the ability to discriminate between active TB disease and latent Mtb infection in the validation cohort (AUC=0.825 [95% confidence interval: 0.683-0.968]; Odds-Ratio=1.10). Right bottom panel shows that a cutoff of 38.8% (of single TNF-α-producing CD4 T cells) was calculated as the optimal threshold.

Figure 14:
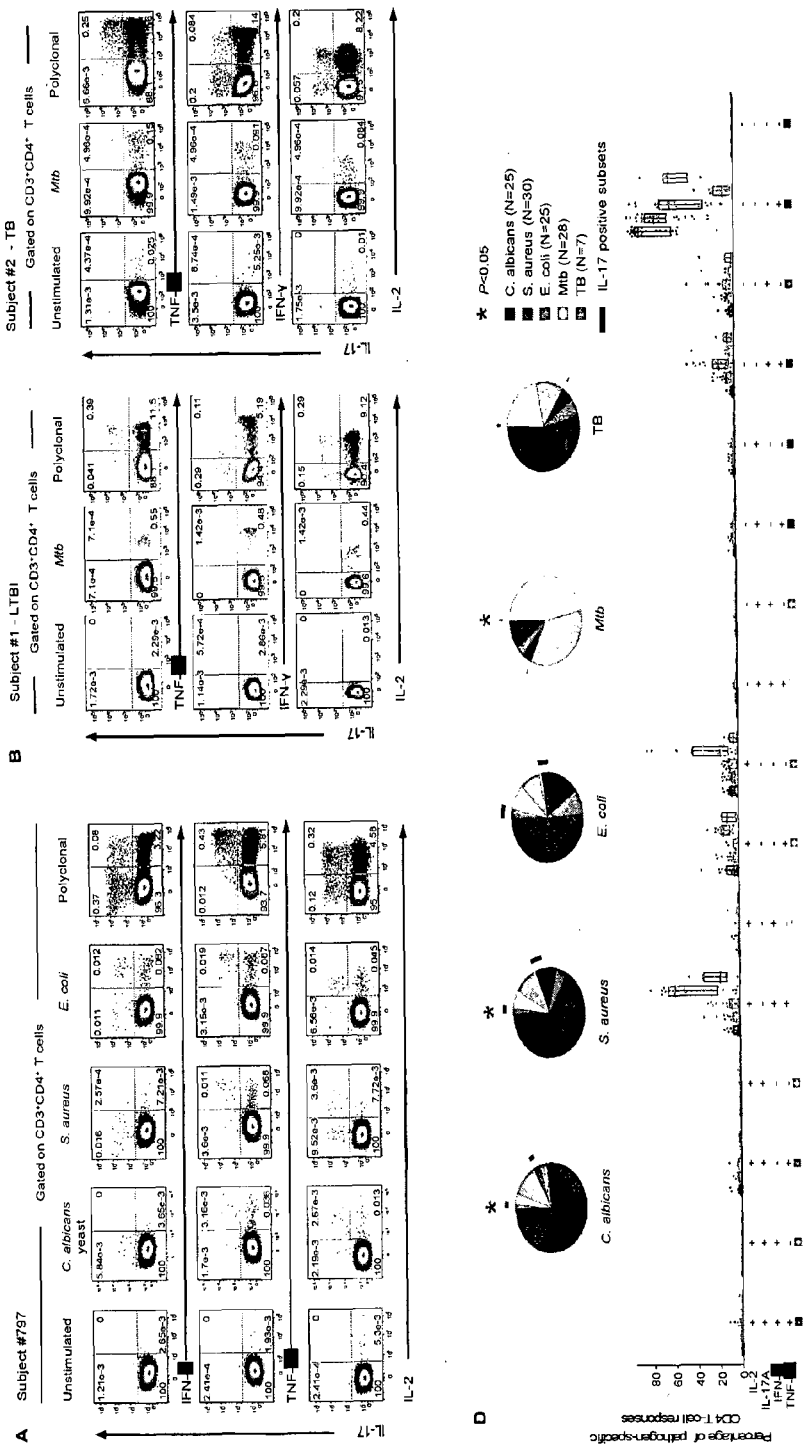

FIG. 14. Lack of ex vivo detection of Mtb-specific IL-17 producing CD4 T cells. (A) Flow cytometric profiles of *C. albicans, S. aureus* and *E. coli*-specific CD4 T cells from a representative healthy subject (Subject #797) and (B) *M. tuberculosis* (Mtb)-specific CD4 T cells from a representative subject with latent Mtb infection (LTBI, Subject #1, left panels) or with active TB disease (TB, Subject #2, right panels) able to produce IL-17, IL-2, TNF-α and IFN-γ. The flow cytometric profiles of unstimulated cells (negative control) and cells stimulated with a polyclonal stimulation (positive control) are also shown. (C) Functional composition of pathogen-specific CD4 T-cell responses. All the possible combinations of the responses are shown on the x axis and the percentage of the functionally-distinct cell populations within the pathogen-specific CD4 T cells are shown on the y axis. Responses are grouped and color-coded on the basis of the combinations of the cytokines produced. The pie charts summarize the data. The black arcs identify IL-17 producing subsets. Stars indicate statistical significance (10000 permutations; P<0.0001). Spots correspond to the fractions of different functionally distinct T-cell populations within the total CD4 T-cells.

Figure 15:
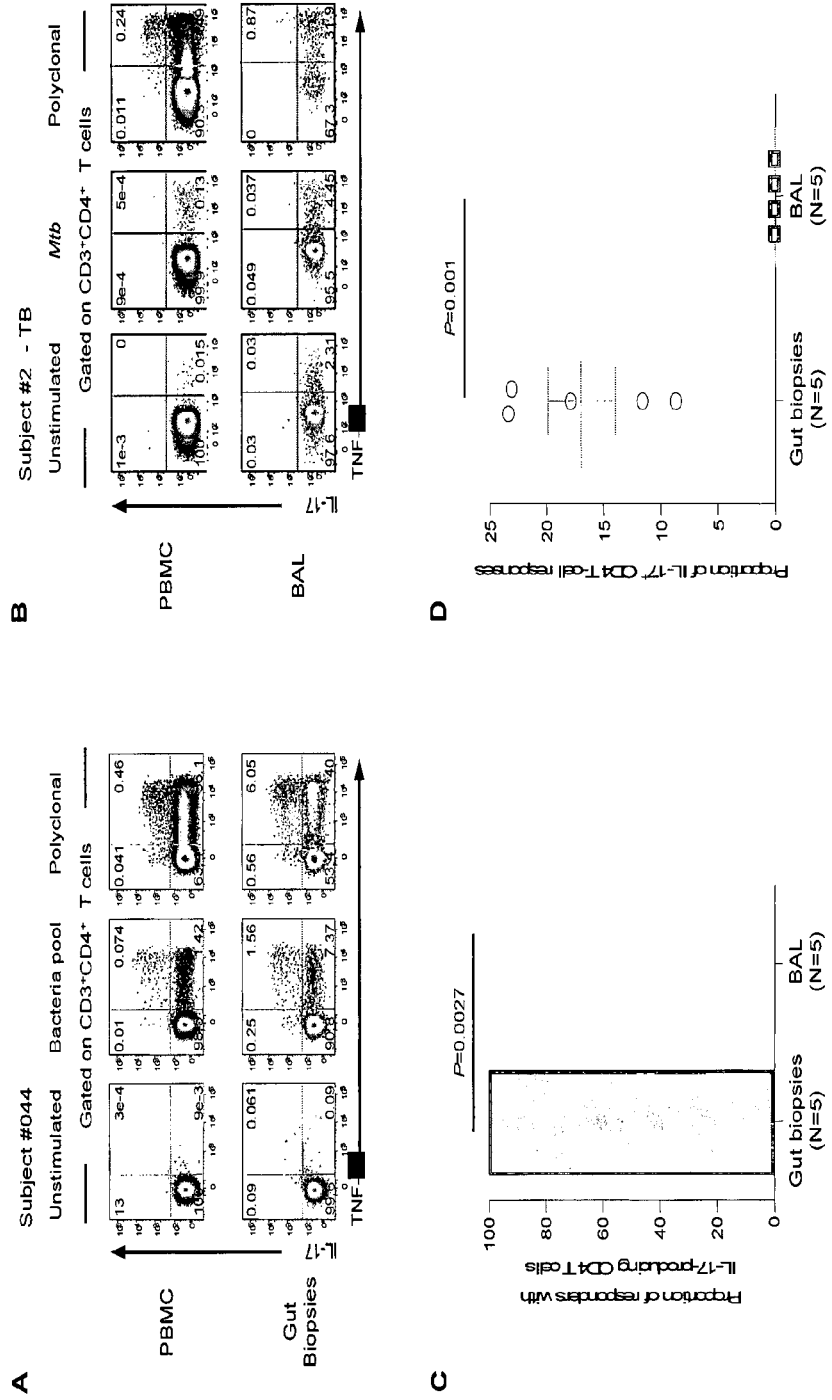

FIG. 15. Mtb-specific CD4 T cells from brochoalveolar lavages (BAL) of TB patients lack immediate IL-17 effector functions. (A) Flow cytometric profiles of extracellular bacteria-specific CD4 T-cell responses from cells isolated from either peripheral blood or gut mucosal tissues from one representative subject (#044). (B) Flow cytometric profiles of Mtb-specific CD4 T-cell responses from cells isolated from either peripheral blood or BAL from one TB patient (Subject #2). (C) Proportion of extracellular bacteria-versus Mtb-specific IL-17 responders from healthy subjects or TB patients detected in gut mucosal tissues or BAL, respectively. Statistical analyses were performed using $\chi^2$ test. (D) Proportion of extracellular bacteria-versus Mtb-specific IL-17 responses among the total CD4 T-cell responses (TNF-α or IFN-γ or IL-2 or IL-17: any responses) from healthy subjects (N=5) or TB patients (N=5) detected in gut mucosal tissues or BAL, respectively. P values were derived from either $\chi^2$ analyses, for comparison of positive proportions or by student t test.

Figure 16:
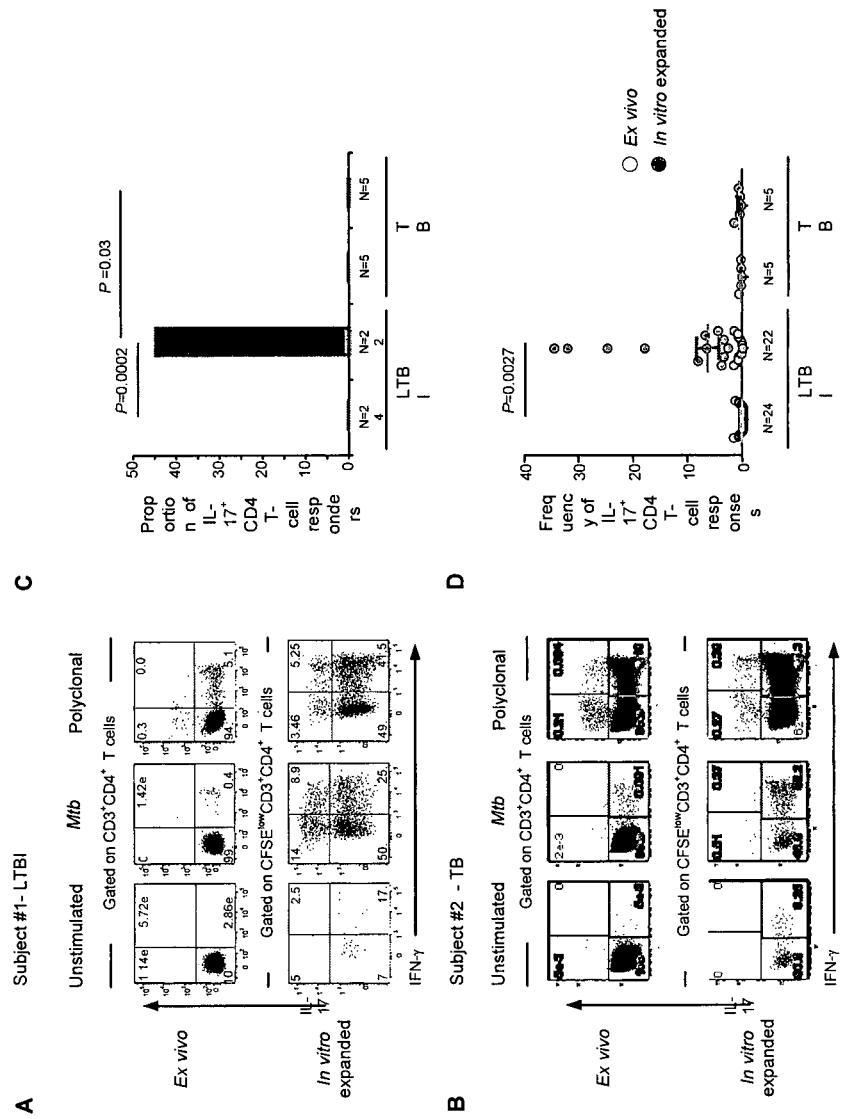

FIG. 16. Acquisition of IL-17 effector function by Mtb-specific CD4 T cells from LTBI subjects but not from TB patients. (A) Flow cytometric profiles of Mtb-specific CD4 T cells either directly ex vivo or following in vitro expansion. Representative LTBI (subject #2279) and TB (patient#GR070193) patients are shown. The flow cytometric profiles of unstimulated cells (negative control) and cells stimulated with a polyclonal stimulation (positive control) are also shown. (B) Proportion of Mtb-specific IL-17 responders from TB patients (N=5) or LTBI (N=14) detected either directly ex vivo or following in vitro expansion. Statistical analyses were performed using $\chi^2$ test. (C) Proportion of Mtb-specific IL-17 responses among the total CD4 T-cell responses (TNF-α or IFN-γ or IL-2 or IL-17: any responses) from TB patients w (N=5) or LTBI (N=14) detected either directly ex vivo or following expansion. P values were derived from either $\chi^2$ analyses, for comparison of positive proportions or by student t test.

Figure 17:
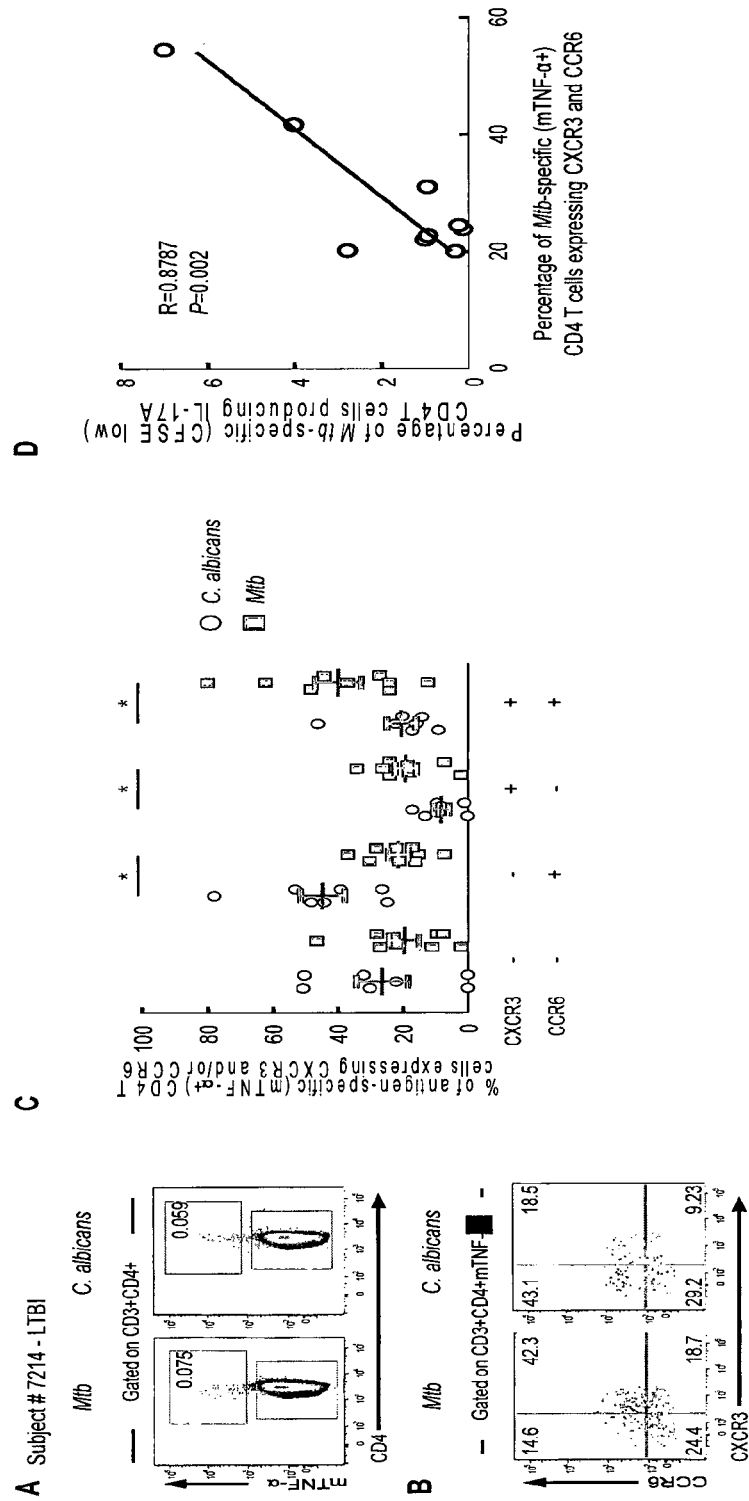

FIG. 17. Acquisition of IL-17A effector function by Mtb-specific CD4 T cells in LTBI subjects directly correlates with the proportion of Mtb-specific CD4 T cells co-expressing CCR6 and CXCR3. (A) flow cytometric profiles of CD4 T cells expressing mTNF-α following Mtb-specific or *C. albicans*-specific stimulation. One representative LTBI subject (subject #5002037214) is shown. Flow cytometric profiles (B) and cumulative data (C) of Mtb-specific and *C. albicans*-specific CD4 T cells expressing CXCR3 and/or CCR6. Blue dots represent antigen-specific CD4 T cells (mTNF-α-expressing CD4 T cells), while the grey density plot represent total CD4 T cells. (D) Acquisition of IL-17A by Mtb-specific CD4 T cells in LTBI subjects directly correlates with the proportion of Mtb-specific CD4 T cells co-expressing CCR6 and CXCR3. P values were derived from student t test or Pearson's correlations.

SUMMARY OF THE DISCLOSURE

This disclosure relates to methods for differentiating between mammals having active Tuberculosis disease and latent *Mycobacterium tuberculosis* (Mtb) infection. In one embodiment, a method for identifying an individual having active Tuberculosis disease by determining the relative percentage of one or more particular types of reactive CD4+ T cells. In certain embodiments, the method comprises isolating mononuclear cells from the mammal, incubating the cells with a peptide derived from *Mycobacterium tuberculosis* (Mtb) (e.g. from proteins such as ESAT-6 or CFP-10), and assaying the CD4+ T-cells for expression of TNFα, IFN-γ, and IL-2. If the relative percentage of mononuclear CD4+ T-cells producing TNFα but not IFN-γ or IL-2 is greater than about 35%, 37.4%, or 38.8%, the individual is identified as having active Tuberculosis disease. Conversely, if the relative percentage of mononuclear CD4+ T-cells producing TNFα but not IFN-γ or IL-2 is less than about 35%, 37.4%, or 38.8%, the individual is identified as not having active Tuberculosis disease but latent Mtb infection. In some embodiments, the relative percentage is determined using flow cytometry.

Also provided are methods for monitoring Tuberculosis disease in an individual being treated for the disease (e.g., by an antibiotic), the method comprising isolating mononuclear cells from the individual 4 weeks, 3 months and/or 6 months after initiation of antibiotic therapy; incubating the cells with a peptide derived from *Mycobacterium tuberculosis* (Mtb); assaying the relative percentage of CD4$^+$ T-cells producing TNFα, IFN-γ, and IL-2; determining the relative percentage of mononuclear CD4$^+$ T-cells producing TNFα and not IFN-γ or IL-2 and, subsequently, either: 1) continuing the current course of antibiotic therapy where the relative percentage of mononuclear CD4$^+$ T-cells producing TNFα and not IFN-γ or IL-2 is lower than about 35%, 37.4%, or 38.8%; or, 2) modifying administration of the antibiotic therapy where the relative percentage of mononuclear CD4$^+$ T-cells producing TNFα and not IFN-γ or IL-2 remains greater than about 35%, 37.4%, or 38.8%. In some embodiments, the methods further comprise repeating these steps. The methods may also comprise administering an antibiotic to an individual having active Tuberculosis disease for 6 months prior to conducting such analyses.

Another measure that may be used to distinguish between latent Mtb infection and active TB disease relates to the expression of IL-17 (e.g., IL-17A, IL-17B, IL17C, IL17D, IL17E and IL17F; preferably IL-17A) by mononuclear cells, such as T cells, especially CD4$^+$ T cells. In certain embodiments, a method for determining the disease status of an individual comprising exposing mononuclear cells of the individual to one or more Mtb antigens and detecting the expression of IL-17, wherein the expression of IL-17 indicates the patient has latent Mtb infection is provided. In one embodiment, the method may include exposing mononuclear cells of the individual to one or more Mtb antigen(s); culturing said mononuclear cells in vitro; restimulating the cultured mononuclear cells; and, assaying supernatant in which the mononuclear cells of step c) were cultured or assaying the cells of step c) to detect IL-17 therein where detection of IL-17 indicates the individual may have latent Mtb infection; and, lack of detection of IL-17 indicates the individual may have active TB disease. In certain embodiments, methods for distinguishing a patient having latent Mtb infection from a patient having active TB disease, the method comprising identifying within a biological sample of a patient having latent Mtb infection, but not in a biological sample of a patient having active TB disease, mononuclear cells that express IL-17 in the presence of Mtb antigen are provided. In some embodiments, the mononuclear cells are peripheral blood mononuclear cells (PBMCs). In certain embodiments, the IL-17 is IL-17A. Some embodiments provide for detection of IL-17 in the culture supernatant of mononuclear cells that have been exposed to one or more Mtb antigens in vitro. Some embodiments provide for detection of IL-17 within the mononuclear cells that have been exposed to one or more Mtb antigens in vitro. In certain embodiments, the mononuclear cells are CD4$^+$ T cells. Methods for treating individuals are also provided. For examples, an individual may be treated for latent Mtb infection if IL-17 in detected using the methods described herein, or treated for active TB disease if IL-17 is not detected using these methods.

Other embodiments of these methods will be evident to the skilled artisan from this disclosure.

DETAILED DESCRIPTION

This disclosure relates to methods for differentiating between mammals having active Tuberculosis (TB) disease and latent *Mycobacterium tuberculosis* (Mtb) infection. This is of particular importance at both the individual (e.g., one mammal) but also population level (e.g., multiple mammals) since only individuals with active TB infection are infectious.

Related methods have been described previously, but none have been found to have the required sensitivity and specificity as those described herein. For example, an IFN-γ ELISpot assay has been described but found not to be useful for differentiating between active TB disease and latent Mtb infection. Other studies have shown that Mtb-specific CD4$^+$ T-cells with latent infection were mostly polyfunctional (e.g., composed of more than 50% of TNFα$^+$IFNγ$^+$IL-2$^+$) while more than 50% of the CD4$^+$ T cells in patients with active TB disease were monofunctional (e.g., TNFα$^+$IFNγ$^-$IL-2$^-$). While a lack of overlap between the functional profiles of CD4$^+$ cells of patients with active TB disease and latent infection suggested that this assay may be useful as a diagnosis tool, it was found not to provide either the required sensitivity or specificity. Those requirements have only now been met by the methods described herein.

Thus, in one embodiment, a method for identifying with sufficient sensitivity and specificity an individual having active TB disease by determining the relative percentage of one or more particular types of reactive CD4$^+$ T cells is provided. In one embodiment, Mtb-specific T-cells may be characterized by isolating the cells from an individual (e.g., having either latent Mtb infection or active TB disease). The cells may then be contacted with Mtb antigens (e.g., peptides). Mtb antigen(s) may be, for example, ESAT-6, CFP-10, and/or tuberculin purified-Protein-Derivative (PPD RT23) and/or derivatives thereof as described herein. The cells may then be assayed to determine the types of cytokines expressed thereby. In some embodiments, the cytokines are IL-2, IFN-γ, and TNF-α. Cytokine expression may be measured using any suitable assay system. Such systems include, for example, immunoprecipitation, particle immunoassays, immunoephelometry, radioimmunoassay, enzyme immunoassay (e.g., ELISA), fluorescent immunoassay (e.g., flow cytometry), and/or chemiluminescent assays. As shown in the Examples below, polychromatic flow cytometry may be especially suitable. Additional assay systems that may be useful in making these determinations are described in, for example, the Examples section.

In other embodiments, methods for identifying with sufficient sensitivity and specificity an individual having active TB disease or latent Mtb infection are provided which involve determining whether the mononuclear cells of the individual produce IL-17 when exposed to Mtb antigen(s) (e.g., ESAT-6, CFP-10, and/or tuberculin purified-Protein-Derivative (PPD RT23) and/or derivatives thereof as described herein). Production of IL-17 in response to exposure to Mtb antigen(s) may be considered an IL-17 effector function. An "immediate" IL-17 effector function is typically one that is observed in mononuclear cells (e.g., PBMCs) after isolation from an individual without further exposure (e.g., in vitro) to Mtb antigen(s). In certain embodiments, an individual having latent Mtb infection may be distinguished from an individual with active TB disease by measuring the expression of IL-17 (e.g., IL-17A, IL-17B, IL17C, IL17D, IL17E and IL17F; preferably IL-17A) by mononuclear cells (e.g., peripheral blood mononuclear cells (PBMC), T cells, and/or CD4$^+$ T cells) of the individual after exposing such cells to Mtb antigen(s). For instance, mononuclear cells obtained from a mammal with latent Mtb infection may be determined to express IL-17 following exposure to Mtb antigen(s) (e.g., in vitro). In contrast, mononuclear cells of a mammal having active TB disease assayed in this way typically do not to express IL-17. Thus, the presence of IL-17-producing mononuclear cells (e.g., CD4$^+$ T cells) in a biological sample of an individual (e.g., after stimulation with Mtb antigen) may allow one to exclude the diagnosis of active TB disease and/or diagnose latent Mtb infection. Such mononuclear cells may be Mtb-specific CD4+ T cells that exhibit an IL-17 effector function, and may be detected in patients with latent Mtb infection but not those with active TB disease. As shown herein, acquisition of IL-17 effector function by Mtb-specific CD4+ T cells may also directly correlate with expression (e.g., co-expression) of CXCR3 and/or CCR6. Thus, this disclosure provides methods for identifying an individual having latent Mtb infection, a mammal having active TB disease, and/or distinguishing an individual having latent Mtb infection from one having active TB disease by detecting in a biological sample of the mammal mononuclear cells (e.g., CD4+ T cells) that express IL-17 in the presence of Mtb antigen(s). Such methods may also be used to predict and/or determine disease status (e.g., latent Mtb infection vs. active TB disease) of a mammal. Such methods typically include assays that comprise exposing mononuclear cells (e.g., CD4+ T cells) to Mtb antigen and detecting IL-17 in the cell culture supernatant and/or within the cells per se (e.g., intracellular), wherein the detection of IL-17 indicates the mammal may have (e.g., has) latent Mtb infection and/or the lack of detection of IL-17 indicates the mammal may have (e.g., has) active TB disease. As described herein, cytokine expression may be measured using any suitable assay system such as, for example, immunoprecipitation, particle immunoassays, immunoephelometry, radioimmunoassay, enzyme immunoassay (e.g., ELISA), fluorescent immunoassay (e.g., flow cytometry), and/or chemiluminescent assays. As shown in the Examples below, polychromatic flow cytometry may be especially suitable. Additional assay systems that may be useful in making these determinations are described in, for example, the Examples section.

Cytokines that may suitable to measurement in the assays described herein include, for example, IFN-γ, TNF-α, IL-2, and/or IL-17, among others. The results derived from the any of assays described herein may be combined to provide added confidence to the diagnosis of active TB disease or latent Mtb infection. The assays may be also combined such that the expression of multiple cytokines and/or cell surface (or other) markers may be measured essentially simultaneously. Cell surface markers that may be suitable for measurement in the assays described herein include, for example, CD3, CD4, CD8, CD19, CD28, CD127, CD154, CD45RA, and/or CCR7, among others. In certain embodiments, expression (e.g., co-expression) of CXCR3 and/or CCR6 may be useful in making the determinations described herein. For cytokine measurement, ELISpot assays may be performed per the instructions of the manufacturer (e.g., Becton Dickinson). Other assay systems that may utilized include, for example, enzyme-linked immunosorbent assay (ELISA), multiplex assays (e.g., arrays, Luminex platform), radioimmunoassay, bioassay, microspheres, intracellular detection (e.g., permeabilization and detection using antibodies), detection of RNA (e.g., messenger RNA (mRNA), using microarrays, polymerase chain reaction, northern blot, and/or similar techniques), flow cytometry, and the like, and/or combinations of such assays. Cell culture supernatants and/or cells per se (e.g., intracellular cytokines) may be assayed for the presence of cytokines. Flow cytometric techniques may also be useful for measuring cytokine expression, which is typically measured by intracellular cytokine staining (ICS). In any such assays, cells may first be assessed for viability by, for example, LIVE/DEAD staining (e.g., Aqua or ViViD from Invitrogen). Typically, the population of cells studied will be at least about 80% viable. In some embodiments, the cells may be at least about any of 85%, 90%, 95%, or 99% viable. Assays are also typically performed in duplicate, triplicate, or quadruplicate. It is standard practice to use software for data procurement and analysis. Statistical analysis is also typically performed (e.g., Fisher's exact test, two-tailed student t test, logistic regression analysis) to provide sensitivity, specificity, positive predictive value (PPV), and/or negative predictive value (NPV). A sensitivity/specificity graph (e.g., ROC-curve graph) may also be generated to determine the probability cutoff. Other cytokines, cell surface markers, and percentages may also be useful in carrying out the methods described herein as would be understood by the skilled artisan.

In carrying out the methods described herein, it may be particularly useful to measure expression of IFN-γ, TNF-α, and IL-2 in circulating peripheral blood mononuclear cells (PBMC) of individuals having active TB disease and/or individuals having latent Mtb infection. In some embodiments, expression of IFN-γ, TNF-α, and IL-2 of CD4+ T cells in such individuals may be assayed (additional cytokines may also be assayed). As shown herein, the expression of TNF-α without substantial co-expression of IFN-γ and/or IL-2 may be used as a measure differentiating between individuals experiencing active Tuberculosis disease and latent Mtb infection. For instance, in some embodiments, greater than about 35% to 40% of circulating CD4+ T cells in an individual with active TB disease will express TNF-α without substantially co-expressing IFN-γ and/or IL-2. In certain embodiments, greater than about 37.4% of circulating CD4+ T cells in an individual with active TB disease will express TNF-α without substantially co-expressing IFN-γ and/or IL-2. And in other embodiments, greater than about 38.8% of circulating CD4+ T cells in an individual with active Tuberculosis will express TNF-α without substantially co-expressing IFN-γ and/or IL-2.

As described in certain embodiments of this disclosure, it may also be particularly useful to measure expression of IL-17 in mononuclear cells (e.g., peripheral blood mononuclear cells (PBMC), T cells, and/or CD4+ T cells) of individuals having active TB disease and/or individuals having latent Mtb infection. In some embodiments, it may be useful to measure and/or compare the expression of IL-17 in mononuclear cells (e.g., after stimulation with Mtb antigen(s)) of individuals suspected to have either active TB disease or latent Mtb infection. In some embodiments, the expression of IL-17 by or within mononuclear cells may be assayed along with other additional cytokines and/or cell surface markers. As shown in the Examples, the expression of IL-17 may be used as a measure differentiating individuals experiencing active TB disease from those with latent Mtb infection. For instance, it has been determined that mononuclear cells that produce IL-17 (e.g., IL-17 producing cells) in the presence of Mtb antigen may be detected in greater than about 50% of individuals with latent Mtb infection while such cells are typically not detected in individuals with active TB disease. Certain of these mononuclear cells also express cell surface markers such as CXCR3 and/or CCR6. As described in the Examples, to carry out such assays, mononuclear cells (e.g., PBMCs) of an individual may be stimulated with Mtb antigen(s) followed by a short term in vitro culture (e.g., typically 5-7 days) and then a short (e.g., 6-hour) re-stimulation (e.g., polyclonal) of the expanded cells. The cells are then assayed to detect IL-17 expression (e.g., in the culture supernatant and/or within and/or upon the cells per se). As shown in the results presented in the Examples, the samples of about half the patients with latent Mtb infection will typically contain IL-17 producing cells while, typically, samples from individuals with active TB disease will not contain any IL-17 producing cells. Thus, the presence of IL-17-producing mononuclear cells (e.g., CD4$^+$ T cells), optionally following exposure of such cells to Mtb antigen(s), may allow one to exclude the diagnosis of active TB disease and/or conclude that the individual may have or has a latent Mtb infection. Other embodiments may also be derived from the Examples described herein.

It is preferred that such measurements are determined to be statistically significant (e.g., P>0.05 for PPV, NPV, sensitivity and specificity). In some embodiments, these assays provide a PPV of at least about 80%, an NPV of at least about 90% (e.g., 92.4%), a sensitivity of at least about 65% (e.g., 66.67%), and a specificity of greater than at least about 90% (e.g., 92.41%). In addition, there should also be concordance between the results of the assay and clinical determinations of, for example, at least about 90%. It is preferred that these assays accurately diagnose active Tuberculosis disease in at least about 80% of cases, preferably greater than about 84% of cases, and even more preferably greater than about 90% of cases. In some instances, the assays may assays accurately diagnose active Tuberculosis disease in at least about 95% or all cases. Other variables may also be measured, and statistics calculated, that may also be useful in using the methods described herein as would be understood by the skilled artisan.

Assays systems that may be used in making these determinations may be, for instance, any of those described in the Examples or otherwise available to one of ordinary skill in the art. Expression of such cytokines may be determined after stimulating PBMCs (e.g., or purified sub-populations thereof) with peptides derived from Mtb. For instance, PMBCs may be stimulated with antigens ESAT-6 (e.g., GenBank NC_000962; MTEQQWNFAGIEAAASAIQGNVTSIHSLLDEGKQSLTKLAAAWGGSGSEAYQGVQQKWDATATELNNALQNLARTISEAGQAMASTEGNVTGMFA (SEQ ID NO.: 1)), CFP-10 (e.g., GenBank NC_000962; MAEMKTDAATLAQEAGNFERISGDLKTQIDQVESTAGSLQGQWRGAAGTAAQA AVVRFQEAANKQKQELDEISTNIRQAGVQYSRADEEQQQALSSQMGF (SEQ ID NO.: 2)), tuberculin purified-Protein-Derivative (PPD RT23) (Statens Serum Institute, Denmark), and/or derivatives thereof. Peptide pools derived from such antigens may also be used to stimulate the cells. For instance, a collection of 9-20 amino acid peptides being adjacent to one another on the parent antigen, or overlapping one another, such at least about all of the amino acid sequences of the parent antigen are represented, may be used to stimulate the cells. In certain embodiments, overlapping 15 amino acid peptides (e.g., "15-mers") may be generated. In some embodiments, the amino acid sequences of such 15-mers may overlap by 1, 2, 3, 4, 5, 6, 7, 8, 9, 10, 11, 12, 13, or 14 amino acids and may represent some or all of the amino acid sequences present in the parent antigen. In certain embodiments, the 15-mers overlap one another by 11 amino acid sequences in series such that together the collection represents part of or the entire parental antigen sequence. For instance, a set of 15-mers derived from ESAT-6 and/or CFP-10 that overlap each other by 11 amino acids where at least part, and optionally all, of SEQ ID NOS.: 1 and/or 2 are represented may be used. The peptides may be placed into culture with PBMCs for a sufficient period of time (e.g., eight hours) prior to further analysis. Positive control assays may include, for example, Staphylococcal enterotoxin B. Other peptides may also be used as would be understood by the skilled artisan.

The methods described herein may also be used to monitor and/or guide therapy. For instance, individuals diagnosed as having active TB disease are typically treated with antibiotics including, for example, isoniazid, rifmpicin (e.g., rifampin), pyrazinamide, ethambutol, and streptomycin. Typically, combinations of such antibiotics are used. A standard antibiotic therapy for treating active TB disease consists of administration of isoniazid, rifmpicin (e.g., rifampin), pyrazinamide, and ethambutol for two months, then isoniazid and rifampicin alone for a further four months. The individual is typically considered cured at six months, although relapse rate of 2 to 3% has been observed. In some instances, treatment with such antibiotics is not completely effective. Additional drugs that may be used include, for example, aminoglycosides (e.g., amikacin (AMK), kanamycin (KM)), polypeptides (e.g., capreomycin, viomycin, enviomycin), fluoroquinolones (e.g., ciprofloxacin (CIP), levofloxacin, moxifloxacin (MXF)), thioamides (e.g., ethionamide, prothionamide), cycloserine, and/or p-aminosalicylic acid (PAS or P), rifabutin, macrolides (e.g., clarithromycin (CLR)), linezolid (LZD), thioacetazone (T), thioridazine, arginine, vitamin D, and/or R207910 (also known as TMC207). For treatment of latent Mtb infection, the standard treatment is six to nine months of isoniazid alone. Other treatment regimens that have been used to treat latent infection include, for example, rifampin for four months, daily administration of isoniazid and rifampin for three months, or administration of rifampin and pyrazinamide for two months (not typically used). Other treatment regimens may also be in use or developed in the future, as would be understood by the skilled artisan.

The treatment of active TB disease and/or latent Mtb infection may be monitored using the methods described herein. Depending on the results, the treatment regimen may be continued or changed as required. For example, it may be beneficial to determine the relative percentage of CD4$^+$ T cells that express TNF-α without substantially co-expressing IFN-γ and/or IL-2 relative to total number of CD4$^+$ T cells in an individual being treated for active TB disease or latent Mtb infection. Where the relative percentage of CD4$^+$ T cells expressing TNF-α without substantially co-expressing IFN-γ and/or IL-2 is greater than about 35% (e.g., 37.4%, 38.8%), it may be concluded that the individual is experiencing active TB disease and that the current treatment regimen may need to be continued and/or modified. Where the relative percentage of CD4$^+$ T cells expressing TNF-α without substantially co-expressing IFN-γ and/or IL-2 is less than about 35% (e.g., 37.4%, 38.8%), it may be concluded that the individual is experiencing latent Mtb infection and that the current treatment regimen is effective and may not need to be continued and/or modified. In some instances, treatment of a patient may be monitored over a period of time (e.g., after one, two, three, or four weeks, or one, two three, four, five six months, or more following the initiation of the antibiotic therapy). During that time period, the relative percentage of CD4$^+$ T cells expressing TNF-α without substantially co-expressing IFN-γ and/or IL-2 may change indicating that the disease status of the individual has changed. In such instances, the treatment regimen may also need to be changed. For example, an increase in the relative percentage of CD4$^+$ T cells expressing TNF-α without substantially co-expressing IFN-γ and/or IL-2 at the six month time point as compared to the four-week time point may indicate a shift from latent Mtb infection to active TB disease, thus requiring a change in the treatment regimen (e.g., from no treatment to a combination of isoniazid, rifmpicin (e.g., rifampin), pyrazinamide, and ethambutol for two months, and/or isoniazid and rifampicin alone for a further four months). Similarly, the methods relating to the measurement of IL-17 may be alternatively, or also, utilized to make such determinations. For example, if is determined that the number of IL-17 producing cells has decreased in an individual (e.g., as determined using the IL-17 related assays described herein) during treatment, it may indicate the individual is beginning to experience active TB disease. Conversely, if the number of IL-17 producing cells increases in an individual (e.g., as determined using the IL-17 assays described herein) during treatment, it may indicate the individual is beginning to experience latent Mtb infection. As mentioned above, the results of TNF-related and IL-17-related assays may be combined to design an appropriate treatment regimen for a particular individual. The TNF-related and IL-17-related assays per se may be also combined such that the expression of multiple cytokines may be measured essentially simultaneously. Thus, the methods described herein may be used to monitor and/or guide treatment of TB disease (e.g., active TB disease) and/or latent Mtb infection. Other embodiments of such methods may also be suitable as would be understood by the skilled artisan.

Also provided herein are kits for detecting the cytokines and/or cell surface (or other) markers in an individual. As described above, various types of detection systems may be utilized to detect the cytokines and/or cell surface (or other) markers in order to diagnose, exclude, and/or distinguish between active TB disease and latent Mtb infection (e.g., ELISpot assays, ELISA, multiplex assays (e.g., arrays, Luminex platform), radioimmunoassay, bioassay, microspheres, intracellular detection (e.g., permeabilization and detection using antibodies), detection of RNA (e.g., messenger RNA (mRNA), using microarrays, polymerase chain reaction, northern blot, and/or similar techniques), flow cytometry, and the like). Kits for detecting TNF-α, IFN-γ, IL-2, and/or IL-17, for example, may include the reagents required to carry out an assay using one or more of the formats available to one of skill in the art, optionally a control reaction (e.g., a known positive or negative reaction (e.g., supernatant known to contain a certain amount of one or more cytokines, cells known to intracellularly express one or more cytokines, and/or either of these known to lack an amount of one more cytokines), and instructions for using the same (e.g., regarding set-up, interpretation of results). The kit may also include reagents used to isolate (e.g., for ficoll-histopaque separation), stimulate (e.g., control antigens, Mtb antigens, phorbol myristate), and/or detect (e.g., optionally labeled antibodies, optionally labeled oligonucleotides, one or more reagents to detect an antibody and/or oligonucleotide) mononuclear cells. The label is typically a detectable label, for example a fluorescent or chromogenic label or a binding moiety such as biotin. The reagents may be free in solution or may be immobilized on a solid support, such as a magnetic bead, tube, microplate well, or chip. The kit may further comprise detection reagents such as a substrate, for example a chromogenic, fluorescent or chemiluminescent substrate, which reacts with the label, or with molecules, such as enzyme conjugates, which bind to the label, to produce a signal, and/or reagents for immunoprecipitation (i.e., protein A or protein G reagents). The detection reagents may further comprise buffer solutions, wash solutions, and other useful reagents. The reagents may be provided in one or more suitable containers (e.g., a vial) in which the contents are protected from the external environment. The kit may also comprise one or both of an apparatus for handling and/or storing the sample obtained from the individual and an apparatus for obtaining the sample from the individual (i.e., a needle, lancet, and collection tube or vessel). Where the assay is to be combined with another type of assay such as PCR, the required reagents for each of such assays (i.e., primers, buffers and the like) along with, optionally, instructions for the use thereof, may also be included. Other types of kits may also be provided, as would be understood by one of ordinary skill in the art.

Throughout this disclosure, exemplification and/or definition of specific terms should be considered non-limiting. For example, the singular forms "a", "an" and "the" include the plural unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Where necessary, ranges have been supplied, and those ranges are inclusive of all sub-ranges there between. The use of the singular may include the plural unless specifically stated otherwise or unless, as will be understood by one of skill in the art in light of the present disclosure, the singular is the only functional embodiment. Thus, for example, "a" may mean more than one, and "one embodiment" may mean that the description applies to multiple embodiments. The phrase "and/or" denotes a shorthand way of indicating that the specific combination is contemplated in combination and, separately, in the alternative.

It will be appreciated that there is an implied "about" prior to the temperatures, concentrations, times, etc. discussed in the present teachings, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

Unless specifically noted in the above specification, embodiments in the above specification that recite "comprising" various components may also be contemplated as "consisting of" or "consisting essentially of" the recited components; embodiments in the specification that recite "consisting of" various components may also be contemplated as "comprising" or "consisting essentially of" the recited components; and embodiments in the specification that recite "consisting essentially of" various components may also be contemplated as "consisting of" or "comprising" the recited components.

All references cited within this disclosure are hereby incorporated by reference in their entirety. While certain embodiments have been described in terms of the preferred embodiments, it is understood that variations and modifications will occur to those skilled in the art. Therefore, it is intended that the appended claims cover all such equivalent variations that come within the scope of the following claims.

EXAMPLES

Example 1

TNF Assays

A. Methods

Patients.

Figure 5:
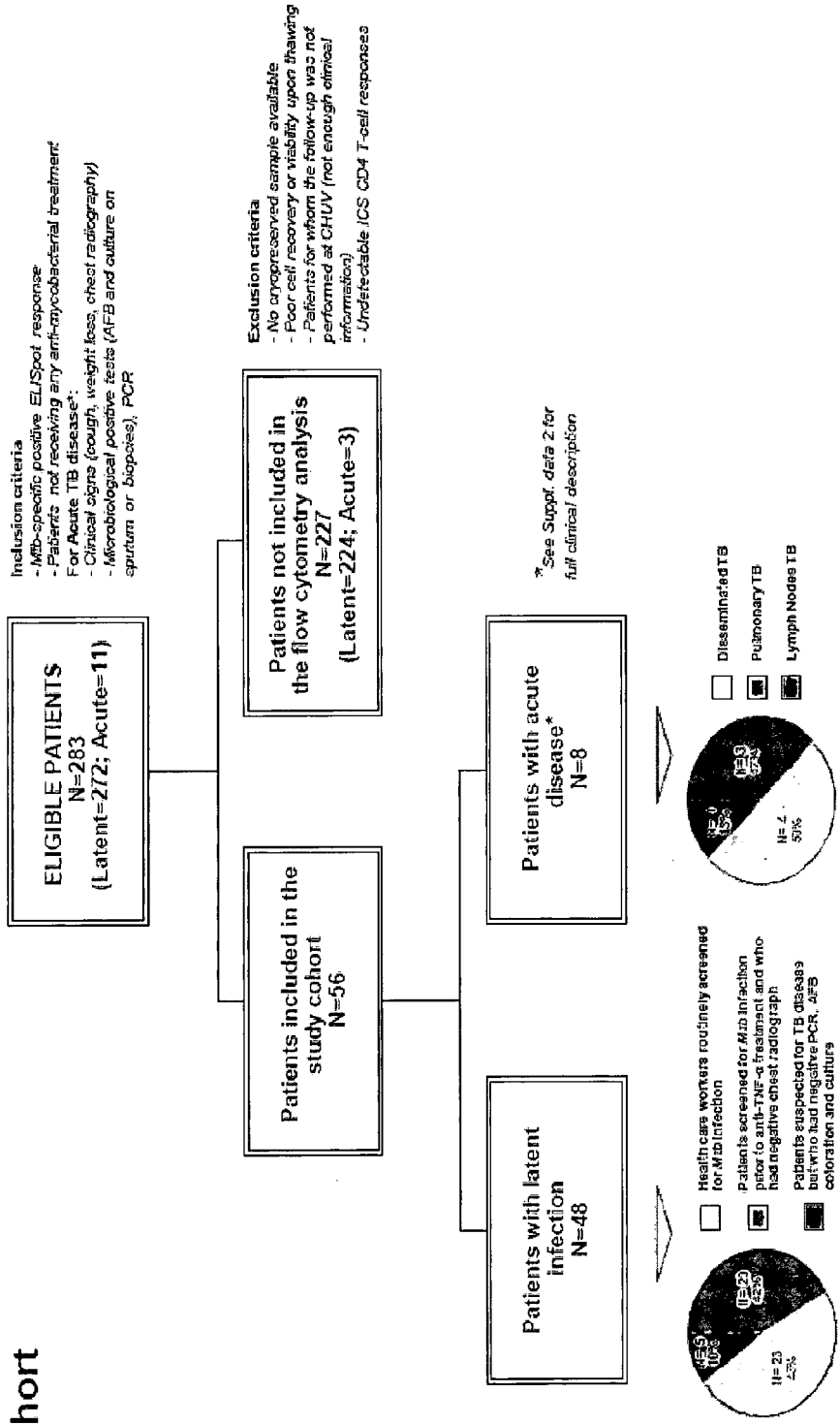
FIG. 5. Flow chart description of patients included in the test cohort.

Participants (n=283) from the test cohort were all recruited at the Centre Hospitalier Universitaire Vaudois (CHUV), Lausanne, Switzerland. These samples were selected based on positive Mtb-specific IFN-γ ELISpot responses routinely performed in the context of the diagnosis for Mtb infection in CHUV. Patients with active TB disease had a diagnosis based on laboratory isolation of Mtb on mycobacterial culture from sputum, broncho alveolar lavage fluid or biopsies and/or TST and/or PCR (see FIG. 5 for full clinical description of each patient). The final diagnosis was given by a clinician after validation of these criteria associated with clinical symptoms. The selection of subjects tested by flow cytometry was based on the availability of cryopreserved material. In addition, samples with low (i.e. <70%) cell recovery and viability upon thawing were discarded from the analyses, in concordance with the current guidelines in the field of intracellular flow cytometric analyses. Furthermore none of these patients was under anti-mycobacterium treatment at the time of the present analyses (FIG. 5). Participants of the validation cohort (n=114) were obtained from two clinical sites (FIG. 10); patients from Switzerland were all recruited from the CHUV and patients from South Africa were recruited from clinics in the public health sector in Cape Town and Worcester, and patients with latent infection from the SATVI (South African Tuberculosis Vaccine Initiative) clinical trials field site in Worcester. Inclusion criteria included: positive Mtb-specific IFN-γ ELISpot responses, between 18 and 80 years old, body weight≥50 kg, hemoglobin≥100 g/L, leukocyte count≥3.0 G/L, platelet count≥75 G/L, and were HIV antibody negative based on a routine rapid HIV test. Patients with active TB had a diagnosis based on laboratory isolation of Mtb on mycobacterial culture from sputum, broncho alveolar lavage fluid or biopsies and/or TST and/or PCR (see FIG. 11 for full clinical description of each patient). The final diagnosis was given by a clinician after validation of these criteria associated with clinical symptoms such as cough or weight loss. Furthermore none of these patients was under anti-mycobacterium treatment at the time of the present analyses. All participants gave written informed consent.

Peptides.

Stimulations were performed using Mtb-derived peptide pools covering ESAT-6 and CFP-10. CFP-10 and ESAT-6 peptides pools are composed of 15-mers overlapping by 11 amino-acids and all peptides were HPLC purified (>80% purity). Tuberculin Purified-Protein-Derivative (PPD RT 23) was purchased from Statens Serum Institute, Denmark.

IFN-γ ELISpot Assays.

ELISpot assays were performed as per the manufacturer's instructions (Becton Dickinson, San Diego, Calif. (BD)). Briefly, cryo-preserved blood mononuclear cells were rested for 8 hours at 37° C. and then 200'000 cells were stimulated with peptide pools (1 µg of each single peptide) in 100 µl of complete media (RPMI+10% FBS) in quadruplicate conditions as described previously. Media only was used as negative control. Staphylococcal enterotoxin B (SEB; 200 ng/ml) was used as positive control on 50'000 cells. Results are expressed as the mean number of spot forming units (SFU) per $10_6$ cells from quadruplicate assays. Only cell samples with >80% viability after thawing were analyzed and only assays with <50 SFU/$10_6$ cells for the negative control and >500 SFU/$10_6$ cells following SEB stimulation were considered as valid. An ELISpot result was defined as positive if the number of SFUs was ≥55 SFU/$10_6$ cells and ≥4-fold the negative control.

Flow Cytometry Analysis.

For intracellular cytokine staining (ICS), cryo-preserved blood mononuclear cells ($1-2\times10^6$) were rested overnight and then stimulated for 6 hours in 1 ml of complete media containing Golgiplug (1 µl/ml, BD) and αCD28 antibodies (Ab) (0.5 µg/ml, BD) as described previously. For stimulation of blood mononuclear cells, peptide pools were used at 1 µg/ml for each peptide. SEB stimulation (200 ng/ml) served as positive control. At the end of the stimulation period, cells were stained for dead cells (LIVE/DEAD kit, Invitrogen), permeabilized (Cytofix/Cytoperm, BD) and then stained with CD3, CD4, CD8, IFN-γ, TNF-α and IL-2 antibodies. All antibodies but CD3 (Invitrogen), and CD4 and CD19 (VWR International) were purchased from BD. Cells were then fixed, acquired on an LSRII SORP (4-lasers) and analyzed using FlowJo 8.8.2 and SPICE 4.2.3 (developed by Mario Roederer, Vaccine Research Center, NIAID, NIH) as previously described. The number of lymphocyte-gated events ranged between $10^5$ and $10^6$ in the flow cytometry experiments shown.

Statistical Analyses.

Comparisons of categorical variables were made using Fisher's exact test. Statistical significance (P values) of the magnitude of ELISpot responses was calculated by unpaired two-tailed student t test using GraphPad Prism 5. Bonferroni correction for multiples analyses was applied. The selection of the optimal(s) parameter(s) to discriminate between cases of latent infection from cases of active disease was performed using a logistic regression analysis followed by a Receiver Operating Characteristic (ROC) curve analysis to evaluate the diagnostic performance of each parameter. Results for the optimal parameter (i.e. single TNF-α) are summarized as a contingency table giving sensitivity, specificity, positive and negative predictive value (PPV and NPV). Analyses provided include a ROC-curve graph and a sensitivity/specificity graph as a function of the probability cutoff.

B. Flow Cytometric Assay for Differentiation of Active from Latent Mtb Infection Mtb-specific T-cells from human patients with latent Mtb infection or active TB disease were analyzed using polychromatic flow cytometry. It was found that single TNF-α$^+$ CD4$^+$ T-cell responses dominated in active disease. This parameter was studied in an independent cohort of 101 patients with blinded TB diagnosis. The results indicated that the sensitivity and specificity of the flow-cytometry-based assay were 67% and 92%, respectively. The concordance between the clinical and the cytokines profile in predicting active TB disease and latent infection diagnosis was confirmed in >90% of cases thus validating the use of the profile of TNF-α$^+$ CD4$^+$ T-cell response in the timely diagnosis of acute TB disease. In the present study, an assay system was developed based upon the cytokine profiles of pathogen-specific T-cells in patients with active TB disease and latent Mtb infection.

Figure 1A:
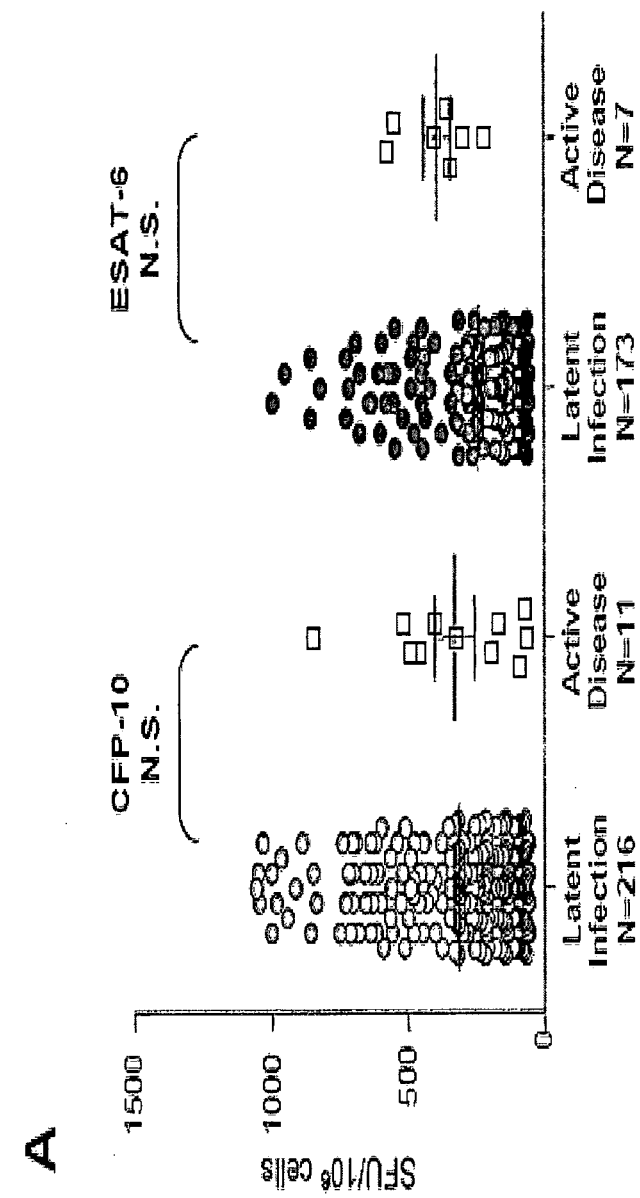
FIG. 1. Quantitative and qualitative analysis of Mtb-specific T-cell responses. A. IFN-γ ELISpot responses following stimulation with ESAT-6 or CFP-10 peptide pools in a cohort of 283 participants with latent Mtb infection (n=272) or active TB disease (n=11, Suppl. Data 1). Shown are the numbers of spot-forming units (SFU) per $10_6$ mononuclear cells. Statistical significance (P values) of the results was calculated by unpaired two-tailed student t test using GraphPad Prism 5. Bonferroni correction for multiples analyses was applied. B. Qualitative analysis of Mtb-specific CD4 T-cell responses by polychromatic flow cytometry. Shown are representative flow cytometry analysis of the functional profile of Mtb-specific CD4 T-cell responses in participants with either latent Mtb infection (Pt#L5, left panels) or active TB disease (Pt#A2, right panels). Profiles are gated on live CD3+ CD4+ T cells and the various combinations of IFN-γ, IL-2 and TNF-α are shown following stimulation with ESAT-6 and CFP-10 peptide pools or PPD. C. Simultaneous analysis of the functional profile of Mtb-specific CD4 T-cells on the basis of IFN-γ, IL-2 or TNF-α production. ESAT-6-, CFP-10- and PPD-specific CD4 T-cell responses are shown from 48 and 8 participants with latent Mtb infection or active TB disease, respectively. Representative examples from Pt#L5 and A#2 shown in FIG. 1B. are also identified. All the possible combinations of the different functions are shown on the x axis whereas the percentages of the distinct cytokine-producing cell subsets within Mtb-specific CD4 T-cells are shown on the y axis. The pie charts summarize the data, and each slice corresponds to the proportion of Mtb-specific CD4 T-cells positive for a certain combination of functions. D. Distribution of CFP-10- and/or ESAT-specific CD4 T-cell responses among patients with latent Mtb infection or active TB disease.

A first cohort of 283 patients with known diagnosis of Mtb infection was enrolled in Switzerland and termed 'test cohort' (FIG. 5). Patients were selected on the basis of positive IFN-γ ELISpot responses against either CFP-10 or ESAT-6 or both. Among the 283 patients, active TB disease was diagnosed in 11 patients based on clinical signs (e.g., cough, weight loss, lymphadenopathy), sputum stain for AFB and culture and PCR for Mtb, and chest radiography$_6$ (see Methods and FIG. 6 for the detailed clinical parameters). The remaining 272 participants were diagnosed with asymptomatic latent Mtb infection. The magnitude of Mtb-specific T-cell responses was first measured by IFN-γ ELISpot following stimulation with CFP-10 or ESAT-6 peptide pools. In agreement with previous studies, Mtb-specific T-cell responses were similar in subjects with latent infection (n=272) and active disease (n=11) (FIG. 1A).

Figure 1B:
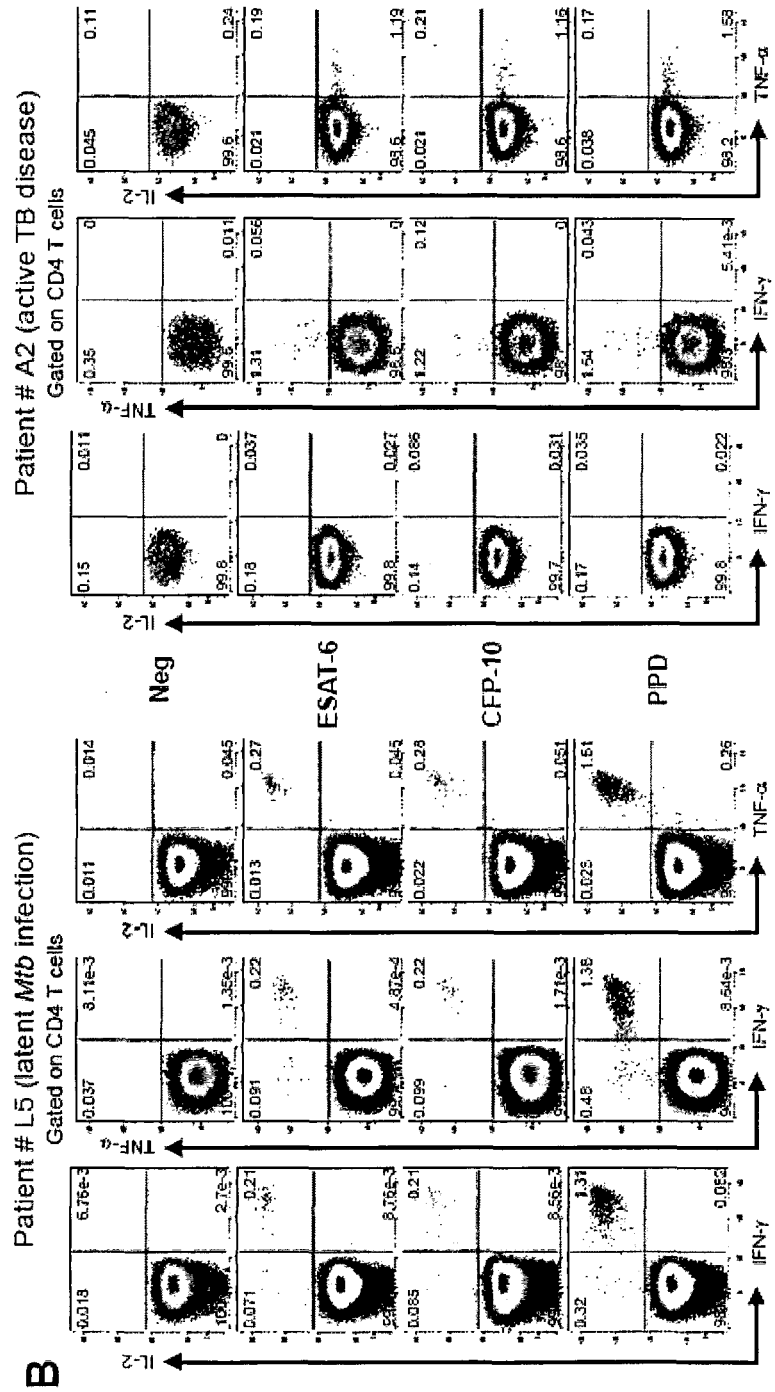
Figure 1C:
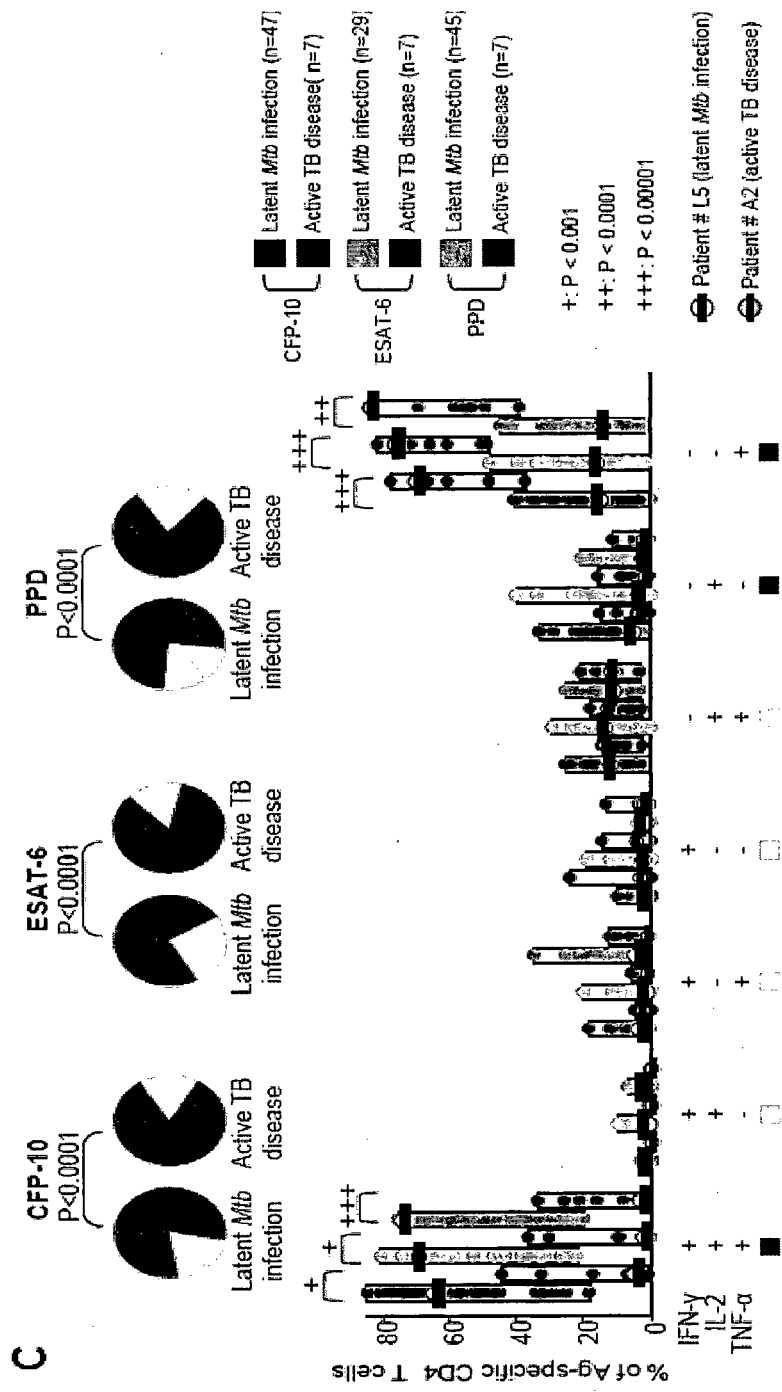
Figure 1D:
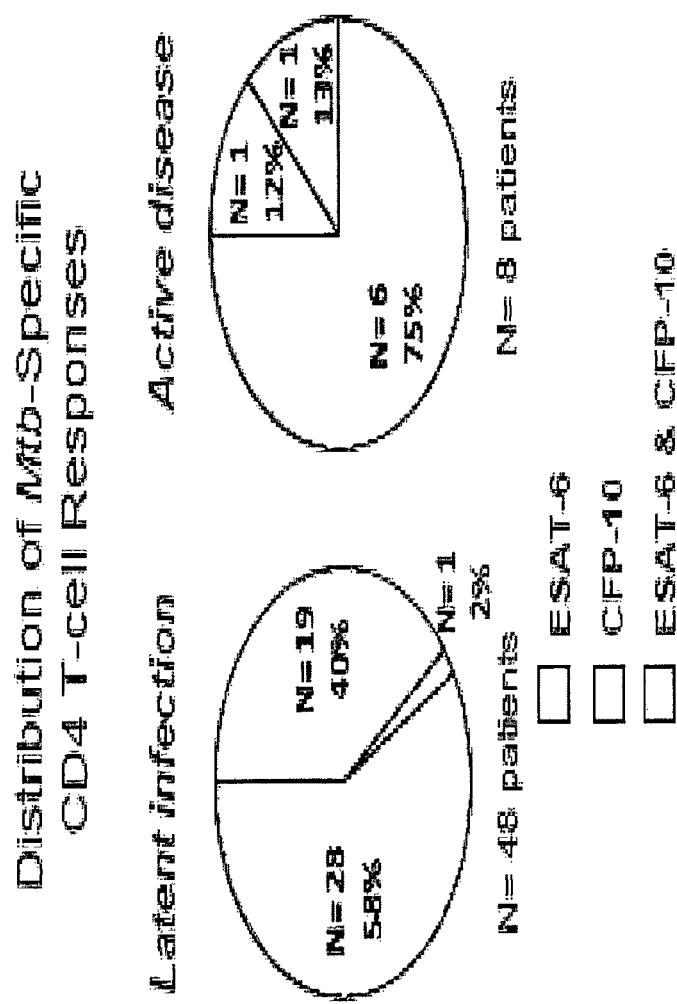
Figure 7:
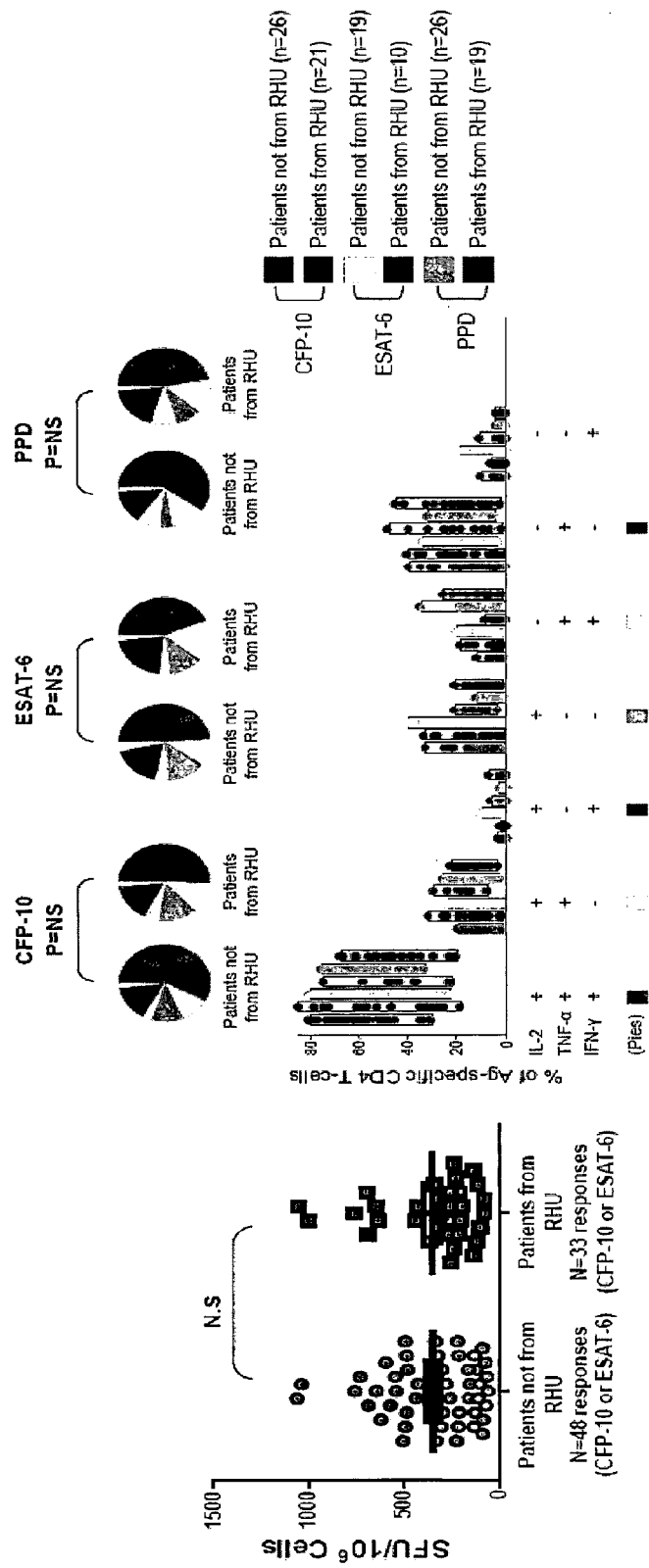
FIG. 7. Analysis of Mtb-specific T-cell responses by IFN-γ ELISpot (left panel) and polychromatic flow cytometry (right panel) from patients screened prior to anti-TNF-α treatment (i.e. patients followed in the department of Rheumatology [RHU]) and the others. All the possible combinations of the different functions are shown on the x axis whereas the percentages of the distinct cytokine-producing cell subsets within Mtb-specific CD4 T-cells are shown on the y axis. The pie charts summarize the data, and each slice corresponds to the proportion of Mtb-specific CD4 T-cells positive for a certain combination of functions.
Figure 8:
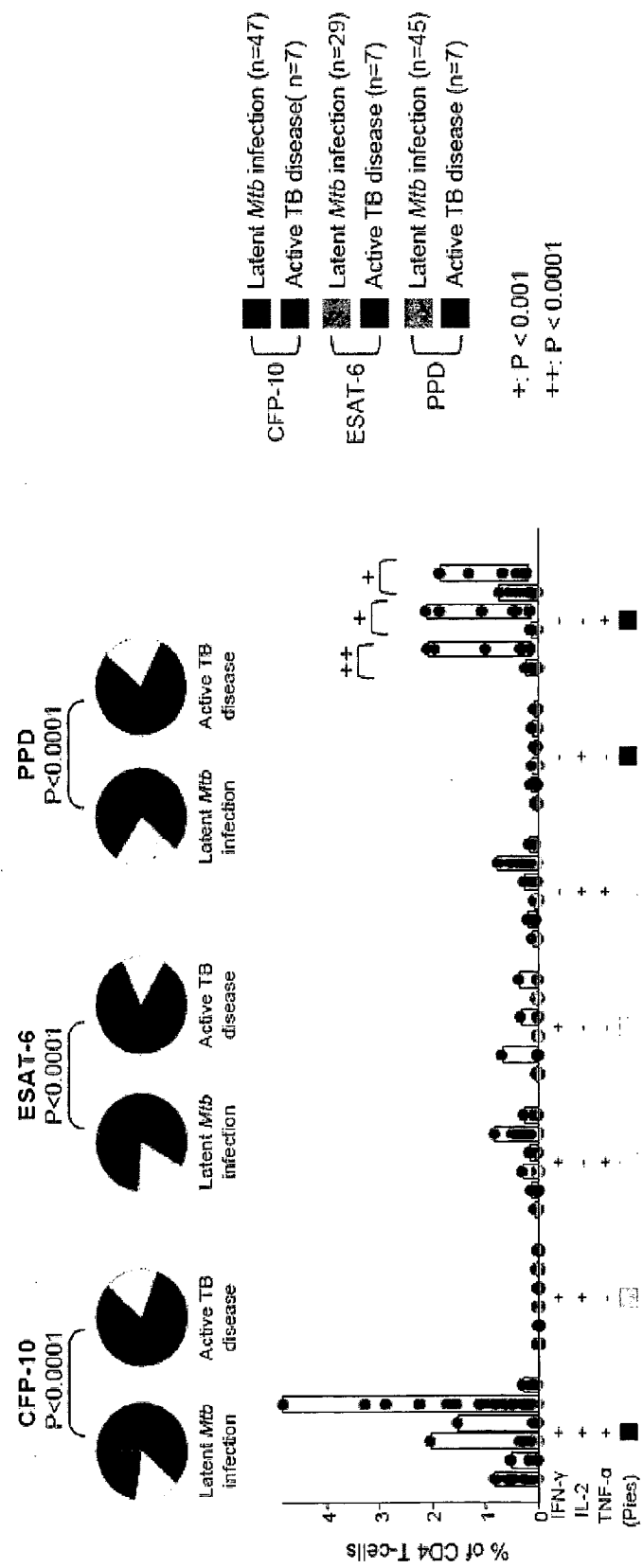
FIG. 8. Analysis of the functional profile of Mtb-specific CD4 T-cells on the basis of IFN-γ, IL-2 or TNF-α production shown in absolute scale. ESAT-6-, CFP-10- and PPD-specific CD4 T-cell responses are shown from 48 and 8 participants with latent Mtb infection or active TB disease, respectively.

The functional profile of Mtb-specific T-cell responses was then assessed using polychromatic flow cytometry. The panel of antigens included a viability marker (CD3); CD4 and CD8 to determine T-cell lineage; and, IL-2, TNF-α and IFN-γ antibodies to comprehensively assess the cytokine functional profile. On the basis of blood specimen availability or quality (see flowchart in Suppl. Data 1), this analysis was performed in 48 patients with latent infection and 8 patients with active disease (i.e. Pt#A1-A8 from Suppl. Data 2). Within the group with latent infection, five were investigated for suspected TB disease, but had negative sputum AFB stain, culture and PCR for Mtb. Twenty-three were health-care workers routinely screened for Mtb infection as part of routine surveillance at the Centre Hospitalier Universitaire Vaudois (CHUV) (FIG. 5). Twenty were investigated for Mtb infection prior to the initiation of anti-TNF-α antibody treatment and had negative chest radiographs (FIG. 5). In agreement with previous studies, Mtb-specific CD4 T-cell responses in participant #L5 with latent Mtb infection were mostly (>70%) polyfunctional (FIG. 1B), i.e., co-producing IFN-γ, IL-2 and TNF-α. In contrast, patient #A2 with active TB disease (FIG. 1B) showed a dominant single TNF-α response (>70% of CD4 T-cells). In these two participants the functional profile of Mtb-specific CD4 T-cells was similar regardless of the stimuli, e.g., ESAT-6 or CFP-10 peptide pools or Tuberculin Purified-Protein-Derivative (PPD, which is a pool of Mtb-derived proteins). Of note, Mtb-specific T-cell responses (analyzed by either IFN-γ ELISpot or flow cytometry) from the 20 patients recruited prior to the initiation of anti-TNF-α antibody treatment were not different from the remaining 28 patients with latent infection (FIG. 7). The striking difference between the functional profile of Mtb-specific CD4 T-cell responses in latent infection versus active disease was confirmed in all 56 patients (e.g., 48 with latent infection and 8 with active disease), in a total of 142 Mtb-specific CD4 T-cell responses (all P<0.0001) (FIG. 1C). Among the 56 patients, most (60-75%) responded to both ESAT-6 and CFP-10 (FIG. 1D). However, 25% of patients with active disease and 40% of patients with latent Mtb infection only responded to one peptide pool. Responses to one peptide pool were mostly against CFP-10 (40% versus 2% ESAT-6) in latent infection whereas were equally distributed between the two peptide pools in active TB disease (FIG. 1D). Furthermore, most patients (>90%) also responded to PPD. Of the 142 responses, 21 were detected in patients with active disease and 121 in patients with latent infection (FIG. 1C). Of note, the differences in the profile of cytokines between active disease and latent infection were confirmed when the data were expressed as absolute frequency of cytokine-producing CD4$^+$ T-cells (Suppl. Data 4). The frequency of single TNF-α-producing CD4$^+$ T-cells was higher in patients with active disease (FIG. 8). These analyses demonstrated that the functional profile, i.e., a polyfunctional or dominant single TNF-α Mtb-specific CD4$^+$ T-cell response, was associated with different degrees of disease activity thus suggesting that it might be instrumental as a diagnostic tool.

The parameter (e.g., functional subset) that was the strongest predictor measure of discrimination between active disease and latent infection was then calculated. For these purposes, since CFP-10 was more frequently recognized than ESAT-6 (FIG. 1D), the analysis was focused on CFP-10-specific CD4 T-cell responses and included ESAT-6-specific CD4$^+$ T-cell responses only when CFP-10 responses were negative. The latter scenario was only observed in one patient with active disease and one patient with latent infection (FIG. 1D).

On the basis of the logistic regression analysis of the multiple functionally distinct T-cell subsets, the proportion of single TNF-α Mtb-specific CD4$^+$ T-cells was found to be the strongest predictor measure of discrimination between active disease and latent infection (AUC=0.995 [95% confidence interval: 0.984-1]; Odds-Ratio=1.35; Suppl. Data 5). In addition, a cutoff of 37.4% of single TNF-α-producing CD4 T-cells was calculated as the value allowing the best (sensitivity of 100% and specificity of 96%) separation between latent infection and active disease (FIG. 9).

A limitation of these results was that the laboratory investigators were not blinded to the diagnosis of latent infection or clinical disease. PBMC were then examined from a second—totally independent—cohort termed 'validation cohort', whose clinical status was blinded to the investigators. Whether the proportion of single TNF-α Mtb-specific CD4 T-cells, and particularly the cutoff at 37.4%, could discriminate between latent infection and active disease was assessed.

One hundred and fourteen participants from both Switzerland (n=72) and Republic of South Africa (RSA, n=42) were enrolled between 2009 and 2010 in order to confirm the functional profile also in persons from a setting with a high TB burden (FIG. 10). Patients from RSA were enrolled from clinics in the public health sector in Cape Town and Worcester, both in the Western Cape province of RSA. Patients from Switzerland included in the validation were enrolled at CHUV and were not included in the test cohort described above. Patients were selected on the basis of the following criteria: positive Mtb-specific IFN-γ ELISpot responses, absence of Mtb-specific treatment, HIV-seronegative and good general health status (see Methods and FIG. 10 for full description). Active TB disease diagnosis in patients from both Switzerland and RSA was based on clinical signs (e.g., cough, weight loss, lymphadenopathy), sputum stain for AFB and culture and PCR for Mtb, and chest radiography$_6$ (see Methods and Suppl. Data 7 for the detailed clinical parameters). Of note, flow cytometry analyses were performed on the 101 patients from the validation cohort with positive Mtb-specific CD4 T-cell responses (FIG. 10).

Figure 2:
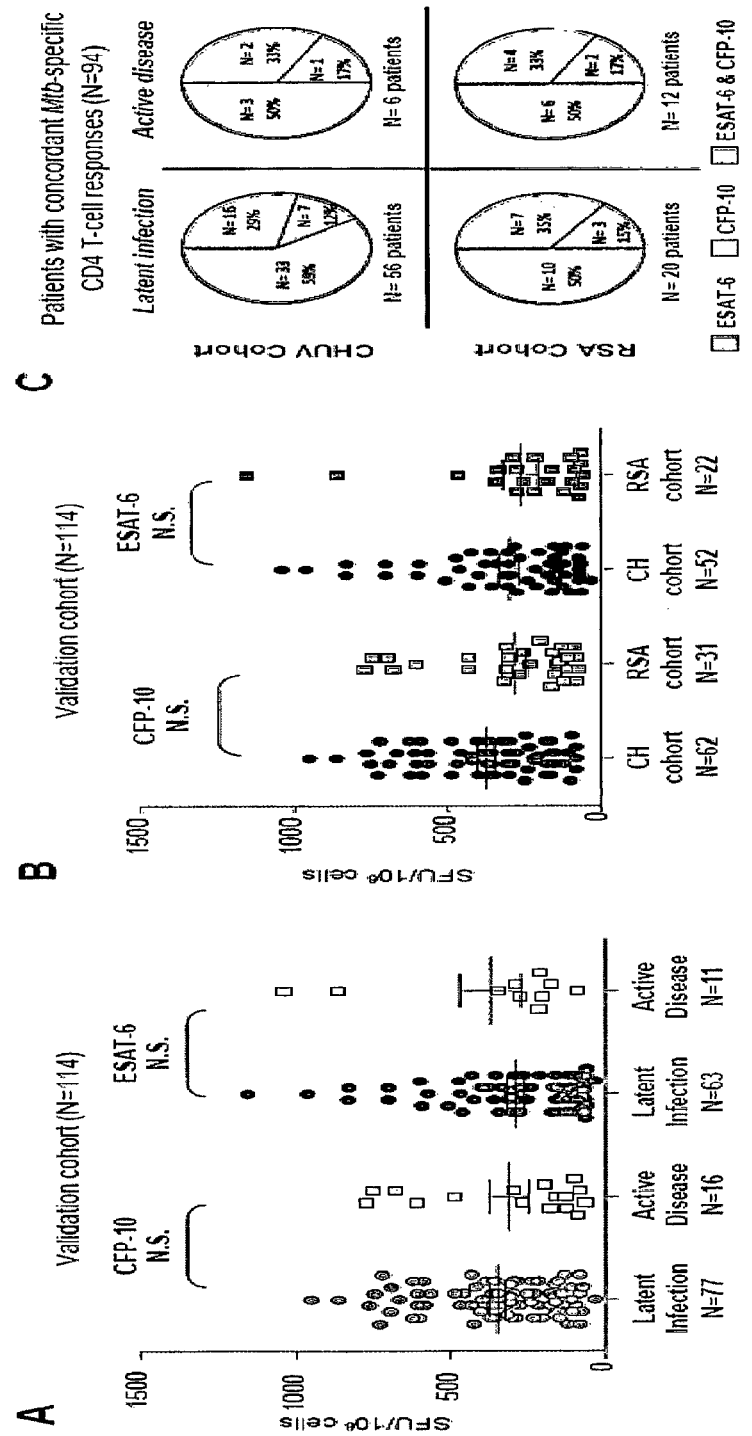
FIG. 2. Analysis of Mtb-specific T-cell responses following unblinding of the clinical status. A. IFN-γ ELISpot responses following stimulation with ESAT-6 or CFP-10 peptide pools. Shown are the numbers of SFU per $10_6$ mononuclear cells. Statistical significance (P values) of the results was calculated by unpaired two-tailed student t test using GraphPad Prism 5. Bonferroni correction for multiples analyses was applied. B. Analysis of Mtb-specific IFN-γ ELISpot T-cell responses in patients enrolled in Switzerland and Republic of South Africa (RSA). C. Distribution of CFP-10- and/or ESAT-specific CD4 T-cell responses among patients from the validation cohort with positive and concordant Mtb-specific CD4 T-cell responses (Suppl. Data 6).

IFN-γ ELISpot and CD4 T-cell specific cytokine expression in response to CFP-10 and/or ESAT-6 were evaluated and data were provided to the biostatistics facility of the CHUV. Later, unblinding of the Mtb clinical status allowed us to confirm that IFN-γ ELISpot responses were not significantly different between latent infection and active disease (FIG. 2A). Of note, the magnitude of Mtb-specific IFN-γ ELISpot responses from patients recruited in Switzerland and RSA were not different (FIG. 2B). In addition, the distribution of CFP-10- and/or ESAT-6-specific CD4 T-cell responses among patients with latent Mtb infection or active TB disease was similar between patients from Switzerland and RSA (FIG. 2C).

Figure 3:
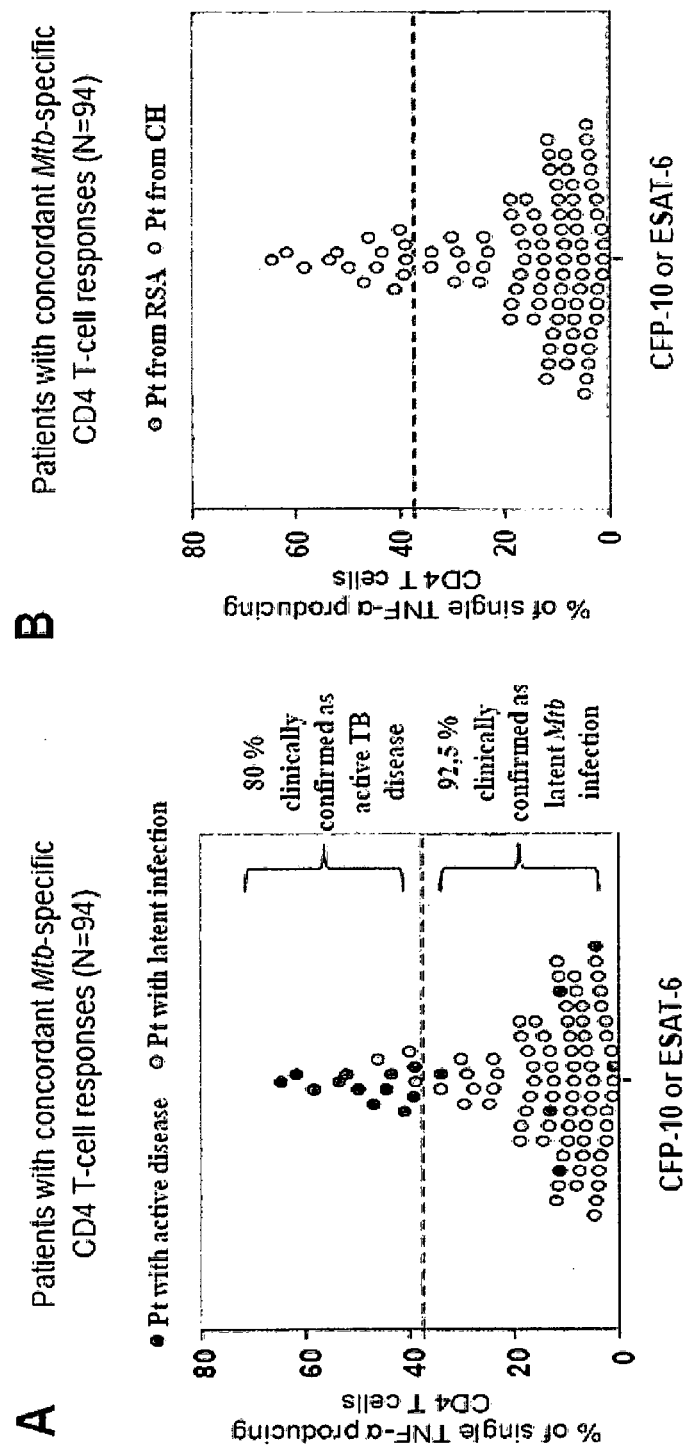
FIG. 3. Percentages of CFP-10- or ESAT-6-specific single TNF-α-producing CD4 T-cells of the 94 patients with concordant responses against CFP-10 and ESAT-6. Dashed line represents the cutoff of 37.4%. A. Patients with active disease or latent infection are identified with blue and red dots, respectively. B. Patients from the Republic of South Africa (RSA) or Switzerland (CH) are identified with orange and green dots, respectively.

With regard to the polychromatic flow cytometric cytokine profile, 15 participants had dominant single TNF-α Mtb-specific CD4 T-cell response, i.e. >37.4%, considered predictive of active disease in the test cohort (FIG. 9). Following unblinding, active disease had been confirmed in 12 of these 15 participants (FIG. 3A). Along the same line, 79 participants had polyfunctional Mtb-specific CD4 T-cells, including a single TNF-α proportion of <37.4%, considered predictive of latent infection in the test cohort (FIG. 9). Following unblinding, 73 out of these 79 participants had latent infection (FIG. 3A). The distribution of patients from Switzerland and RSA is also shown in FIG. 3B. Of note, among the 94 aforementioned subjects (e.g., 15 with a profile of active disease and 79 with a profile of latent infection), CFP-10- and ESAT-6-specific CD4$^+$ T-cell responses, when both positive, were concordant (e.g., both either above or below the cut-off of 37.4% of single TNF-α). In these 94 concordant cases the data of CFP-10-specific CD4$^+$ T-cell response were considered for the analyses and ESAT-6-specific CD4$^+$ T-cell response were only included when CFP-10 responses were negative (FIG. 3A). Seven out of 101 (e.g., 6.9%) participants studied showed discordant CD4$^+$ T-cell responses to ESAT-6 and CFP-10 peptide pools (e.g., one response >37.4% and the other response <37.4%) and were therefore excluded from the analysis (FIG. 12). Of note, the performance of the test on the cohorts from Switzerland and RSA were not significantly different (P>0.05 for Positive Predictive Value (PPV), Negative Predictive Value (NPV), sensitivity and specificity), thus providing evidence that the combined analysis of Swiss and RSA cohorts is valid. On the basis of the analysis on the combined cohorts, the global performance of the assay was: PPV=80%; NPV=92.4%; Sensitivity=66.67% and Specificity=92.41% (FIG. 13). Overall, the concordance between the clinical and the cytokines profile in predicting diagnosis was confirmed in 90% of cases. Of note, when patients with discordant ESAT-6 and CFP-10 responses were also included in the analysis, the accurate diagnosis was determined in 84% of subjects.

The percentage of Mtb-specific single TNF-α producing CD4$^+$ T-cells was studied to determine if it was the parameter with the strongest predictive value of the clinical status in the validation cohort. On the basis of the logistic regression analysis of the multiple functionally distinct T-cell subsets, the proportion of single TNF-α Mtb-specific CD4 T-cells indeed resulted to be the strongest predictor measure of discrimination between active disease and latent infection (AUC=0.825 [95% confidence interval: 0.683-0.968]; Odds-Ratio=1.10; FIG. 13). In addition, a cutoff of 38.8% (as compared to 37.4% obtained in the test cohort) of single TNF-α-producing CD4$^+$ T-cells was calculated as the value allowing the best separation between latent infection and active disease (FIG. 13).

Figure 4:
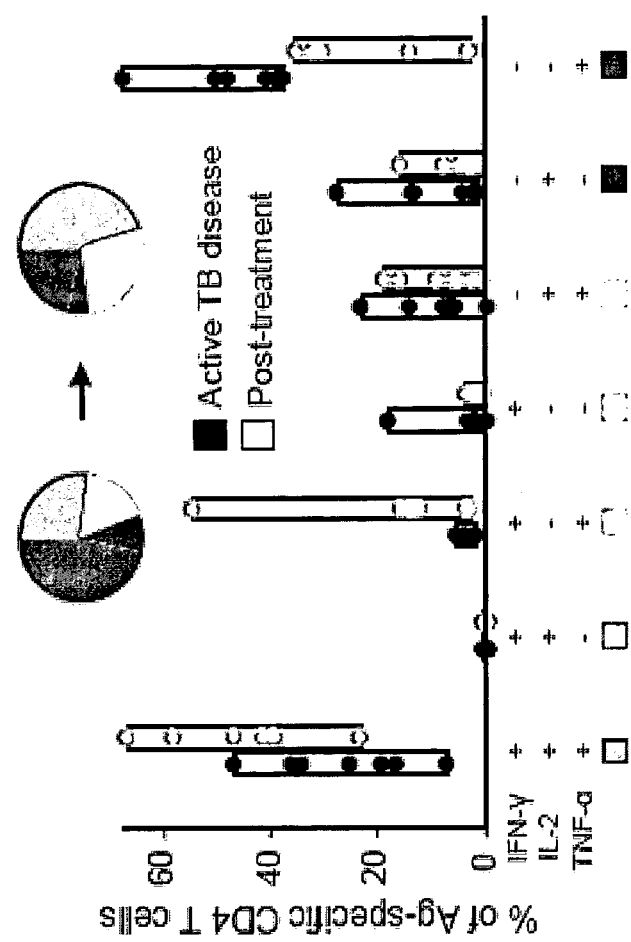
FIG. 4. Longitudinal analysis of the percentage of Mtb-specific single TNF-α-producing CD4 T-cells from 5 patients analyzed during untreated active TB disease and then post-TB treatment. Shown is the full functional profile (SPICE analysis) on the basis of IFN-γ, IL-2 and TNF-α production of a total of 7 Mtb-specific CD4 T-cell responses. All the possible combinations of the different functions are shown on the x axis whereas the percentages of the distinct cytokine-producing cell subsets within Mtb-specific CD4 T-cells are shown on the y axis. The pie charts summarize the data, and each slice corresponds to the proportion of Mtb-specific CD4 T-cells positive for a certain combination of functions.

Of interest, we also had the opportunity to investigate five participants during untreated active TB disease and then post-TB treatment (FIG. 4). In agreement with the above data, the percentage of single TNF-α-producing CD4$^+$ T-cells was >37.4% in patients with active TB disease. A shift to a polyfunctional profile (single TNF-α producing CD4 T-cells<37.4%) of Mtb-specific CD4$^+$ T-cell response was observed following therapy and transition to latent infection in all the 5 participants (FIG. 4).

The association between different functional profiles of T-cell responses and disease activity is consistent with the current paradigm in antiviral immunity where virus-specific T-cell responses endowed with only effector functions such as IFN-γ and/or TNF-α production were found in patients with active virus replication and active disease. In contrast, polyfunctional responses, i.e., comprising cells producing IL-2 in addition to effector/inflammatory cytokines, were present in patients with controlled virus replication and no signs of clinical disease.

The fundamental role of TNF-α, in the control of Mtb infection in both humans and mice is well established and this is also supported by the increased risk of Mtb reactivation in rheumatoid arthritis participants receiving anti-TNF-α therapy. However, the dominant single TNF-α CD4$^+$ T-cell response observed during active TB disease may rather reflect the elevated degree of inflammation associated with active TB disease and therefore may be a marker of excessive inflammation and not of protection.

A recent study has shown that a neutrophil-driven interferon-inducible gene profile correlated with active TB disease and it was also found in about 10% of people with latent infection. Since about 10% of patients with latent infection go on to develop the active disease it was suggested that the biomarker may be useful in both prognosis and diagnosis. There was no evidence in this study of a T cell-driven TNF-α-inducible gene profile correlated with active TB disease. However, the transcriptional profile was assessed on total unstimulated blood cell populations. It was therefore not suitable for evaluating the transcriptional profile in T-cell populations that needs to be performed on stimulated T-cells.

These results indicate that analysis of cytokines profiles in Mtb-specific CD4$^+$ T-cells by polychromatic flow cytometry is a strong immunological measure discriminating between active and latent Mtb infection. Therefore, polychromatic flow cytometry is a novel and reliable laboratory tool for the timely diagnosis of active Mtb infection.

Example 2

IL-17 Assays

A. Material and Methods
Study Groups.

Thirty healthy volunteers were recruited in this study. Blood samples were obtained at the local blood bank (Lausanne, Switzerland). In addition, 5 subjects with normal colonoscopic findings that underwent routine colonoscopic investigations were recruited and provided gut biopsies as well as peripheral blood. In addition, 28 subjects with latent Mtb infection and 10 patients with active TB disease were also recruited. Furthermore, 5 patients with active TB disease also provided BAL specimens. Inclusion criteria were based as described above. Briefly, all subjects were selected based on positive Mtb-specific IFN-γ ELISpot responses against peptide pools encompassing ESAT-6 (early secreted antigenic target-6 kDa) and/or CFP-10 (culture filtrate protein-10 kDa), allowing discrimination between infection and vaccination. Subjects with latent Mtb infection (LTBI) were either health-care workers routinely screened or were investigated for Mtb infection prior to the initiation of anti-TNF-α antibody treatment and had negative chest radiographs. Patients with active TB disease had a diagnosis based on laboratory isolation of Mtb on mycobacterial culture from sputum, broncho alveolar lavage fluid or biopsies and/or TST and/or PCR and final diagnosis was given by a clinician after validation of these criteria associated with clinical symptoms. Furthermore none of these patients was under anti-mycobacterium treatment at the time of the present analyses. These studies were approved by the Institutional Review Board of the Centre Hospitalier Universitaire Vaudois and informed written consent was obtained from each volunteer.

Antigen Preparation.
S. aureus, S. pneumoniae, P. aeruginosa, K. Pneumonia, S. typhi and E. coli were grown in tryptic soy broth (TSB, BD Biosciences) at 37° C., washed and heat-inactivated by incubation for 2 h at 56° C. C. albicans yeasts were cultured at 30° C. in yeast extract peptone dextrose (YEPD) for 5 h. To promote hyphae formation, C. albicans were cultured for an additional 5 h in RPMI (Invitrogen) containing 10% FCS (Invitrogen), and hyphal formation was monitored by microscopy. C. alicans yeast and hyphae were heat-inactivated by incubation for 2 h at 56° C. Following inactivation, antigens were lyophilized and re-suspended at 10 mg/ml in 0.9% NaCl. Mtb-derived CFP-10 and ESAT-6 peptides pools are composed of 15-mers overlapping by 11 amino-acids encompassing the entire sequences of the proteins and all peptides were HPLC purified (>80% purity).

Mononuclear Cells Isolation.
Mononuclear cells were isolated either from peripheral blood using ficoll-histopaque separation, or following collagenase digestion of gut biopsies, or from BAL. Briefly, mononuclear cells were isolated from gut biopsies collected in the rectum of subjects with normal colonoscopic findings that underwent routine colonoscopic investigations.

Colonoscopies were performed under conscious sedation with midazolam and pethidine in moderate doses with a Pentax colonoscope type EC 3890 Fi (Pentax, Japan). Tissue samples (N=5) were collected with Radial Jaw 4 forceps (Boston Scientific Corporate Natick, Mass., USA). Mononuclear cells were isolated following type II-S collagenase digestion (Sigma; 0.5 mg/ml; 37° C.; 90 minutes) in complete RPMI (10% fetal calf serum, 100 μg penicillin, 100 unit/ml streptomycin). BAL were performed in patients with active TB disease (N=5) as previously described. Briefly, bronchoalveolar fluids were centrifuged (10 min, 300 g) and resuspended in complete RPMI.

Assessment of Ex Vivo CD4 T-Cell Responses.

Mononuclear cells ($10^6$ cells) isolated from peripheral blood were stimulated overnight in 1 ml of complete RPMI containing Golgiplug (BD Biosciences; 1 μg/ml) as described. PBMCs isolated from healthy subjects were stimulated with 10 μg/ml of heat-inactivated *C. albicans* yeast or hyphae, or $5\times10^7$ CFU/ml of bacteria, while mononuclear cells isolated from both peripheral blood and BAL from LTBI or TB patients were stimulated with ESAT-6 and/or CFP-10 peptide pools (1 ms/ml). Mononuclear cells isolated from gut biopsies were stimulated with a pool of bacteria-derived antigens (*S. aureus, S. pneumonia, P. aeruginosa, K. pmeunomiae, S. typhi, E. coli;* $5\times10^7$ CFU/ml). As positive control, cells were stimulated with *Staphylococcus* enterotoxin B (SEB; 100 ng/ml; Sigma).

Assessment of In Vitro Expansion of CD4 T-Cell Responses.

Mononuclear cells were re-suspended at $10^6$/ml in PBS and incubated for 7 min at 37° C. with 0.25 μM 5,6-carboxyfluorescein succinimidyl ester (CFSE, Invitrogen) as previously described. The reaction was quenched with one volume of FCS. Subsequently, cells were washed, cultured in 4% human AB serum (Institut de Biotechnologies Jacques Boy) RPMI, and as described above. After five days of in vitro T-cell expansion, cells were washed and replated in complete medium for 18 h of rest. Cells were then re-stimulated for 6 h with phorbol myristate acetate (PMA; Sigma; 100 ng/ml) and ionomycin (Sigma; 1 μg/ml) in the presence of Golgiplug (1 μg/ml).

Assessment of CXCR3 and CCR6 Expression on Antigen-Specific CD4 T Cells Using Membrane-Bound TNF-α.

Blood Mononuclear cells ($10^6$ cells/ml) were stimulated (6 hours) or not with heat-inactivated *C. albicans* yeast (10 μg/ml) or ESAT-6 or CFP-10 peptide pools (1 μg/ml) in complete RPMI containing TAP1-0 (10 μM; Calbiochem) and PE-CY7-conjugated anti-TNF-α as described. At the end of the incubation period, cells were stained with antibodies directed to CD3, CD4, CCR6 and CXCR3 and percentage of CXCR3 and CCR6 expression on antigen-specific CD4 T cells were assessed by flow cytometry.

Flow Cytometry Analyses.

To assess antigen-specific CD4 T-cell responses, the following Abs were used: CD4-APC-H7 (clone SK3); CD8-PerCP-Cy5.5 (SKI); CD3-ECD (UCHT1); IFN-γ-AF700 (B27); IL-2-PE (MQ1-17H12); TNF-α-PECY7 (Mab11), IL-17A-AF-647 (eBio64DEC17), CXCR3-APC (TG1/CXCR3) and CCR6-PE (11A2). All Abs were purchased from BD Biosciences except IL-17A (eBioscience), CD3-ECD (Beckman Coulter) and CXCR3-APC (Biolegend). Furthermore, dead cells were excluded using the violet LIVE/DEAD stain kit (Invitrogen). At the end of the stimulation period, cells were washed, permeabilized (cytofix/cytoperm solution; BD Biosciences) and stained as previously described [30]. Data were acquired on an LSRII three-laser (488, 633 and 405 nm) and analyzed using FlowJo version 8.8.6 (Tree Star inc.). Analysis and presentation of distributions was performed using SPICE version 5.1, downloaded from: http://exon.niaid.nih.gov/spice. The number of CD4-gated events was above $2\times10^5$ in the flow cytometry experiments shown. Concerning the assessment ex vivo CD4 T-cell responses, an individual was considered as a positive responder for a particular antigen, when as least one cytokine was positive. For blood analyses, the positivity of each cytokine was determined as follows: the cytokine frequency obtained in the sample must exceed the threshold (set as the mean of the controls for all donors+2 SD (e.g., TNF-α: 0.032; IFN-γ: 0.017; IL-2: 0.018; IL-17A: 0.010)) and ≥3 times the value obtained in the corresponding individual's control. For tissues analyses, the positivity of each cytokine was determined as follows: the cytokine frequency obtained in the sample must be ≥3 times the value obtained in the corresponding individual's control. Concerning, in vitro expanded CD4 T-cell responses, the percentage of proliferating CD4 T cells, i.e. $CFSE^{low}$ cells was determined in the $CD3^+CD4^+$ T-cell population. The criteria for scoring as positive the proliferating cell cultures included: a) percentage of $CFSE^{low}$ cell>1% after subtraction of background (percentage of $CFSE^{low}$ cells in unstimulated cell cultures) and b) stimulation index (SI)>3. The SI is calculated as the ratio between stimulated versus unstimulated cell cultures. The positivity of each cytokine was determined as follows: the cytokine frequency obtained in the sample must ≥3 times the value obtained in the corresponding individual's control.

Statistical Analyses.

P values were derived from either $\chi^2$ analyses, for comparison of positive proportions, or One-way ANOVA (Kruskal-Wallis test), followed by student t test. When applicable, Bonferroni correction for multiples analyses was applied.

B. Differentiation of Active from Latent Mtb Infection

In the present study, the presence of IL-17A-producing Mtb-specific CD4 T cells has been studied in 10 patients with active TB disease and 28 patients with Mtb latent infection. Since IL-17A-producing CD4 T-cell responses are commonly ascribed to extracellular pathogen-specific CD4 T-cell responses, we have systematically compared Mtb- to extracellular pathogen-specific CD4 T-cell responses from 30 healthy individuals.

The functional profiles of Mtb-specific and extracellular pathogen-specific CD4 T-cell responses were investigated ex vivo by intracellular cytokine staining. In particular, the ability of pathogen-specific CD4 T cells to produce IL-17A, in addition to IFN-γ, TNF-α and IL-2 was assessed. In-depth analysis of pathogen-specific CD4 T-cell responses demonstrated that the global functional profile of T-cell responses against the Mtb in LTBI or TB subjects and for extracellular pathogens in healthy subjects were all significantly different from each other (P<0.05 (except TB versus *E. coli* (P>0.05)). In particular, Mtb-specific Th17 cells were not detected ex vivo in LTBI (n=28) or TB patients (n=7). Consistently with our previous study, Mtb-specific CD4 T-cell responses were mostly composed of triple TNF-α/IFN-γ/IL-2 or of single TNF-α-population in LTBI or TB subjects, respectively (FIG. 14). In contrast, extracellular pathogen-specific CD4 T-cell responses were dominated by single TNF-α-producing cells (76% for *C. albicans,* 73% for *S. aureus* (Gram-positive bacteria) and 57% for *E. coli* (Gram-negative bacteria)) (FIGS. 14B and C). However, in contrast to Mtb-specific CD4 T-cell responses, Th17 cells were frequently detected in response to extracellular pathogens (ranging from 20% to 50%), but represented a consistent but minor component of the responding CD4 T cells.

Since preferential accumulation of antigen-specific T cells at the site of pathogen-replication/exposure is well established, whether Mtb-specific IL-17A-producing CD4 T cells in TB patients could be present in lung tissue was investigated. To address this issue, Mtb-specific CD4 T-cell responses were assessed on cells isolated from peripheral blood and from bronchoalveolar fluids. As an internal control, extracellular bacteria-specific T-cell responses were also assessed on cells isolated from both peripheral blood and from gut mucosal biopsies from healthy subjects. As shown in the representative flow cytometric profiles, bacteria-specific IL-17A-producing CD4 T cells were consistently detected in both blood and gut mucosal tissues in healthy individuals (FIG. 15A), whereas IL-17A-producing Mtb-specific CD4 T-cell responses from cells isolated from either peripheral blood or BAL were not detected (FIG. 15B). Cumulative analyses confirmed the lack of Mtb-specific as compared to bacteria-specific Th17 responses in the relevant tissue (i.e. BAL versus gut mucosa) (P=0.0027; FIG. 15C). Consistently, the frequencies of bacteria-specific Th17 cells in gut biopsies was also significantly increased as compared to Mtb-specific Th17 cells in BAL (P=0.001; FIG. 15D). These data indicate that (ex vivo) Mtb-specific CD4 T cells of TB patients lack immediate IL-17A effector functions also in BAL.

However, Mtb-specific CD4 T cells in LTBI subjects, but not in TB patients, were found to acquire IL-17A effector function (e.g., meaning that "Th17" cells were detectable) following antigen-specific in vitro expansion. CFSE-labeled PBMCs from LTBI subjects or TB patients were stimulated with Mtb-derived antigens for six days. As control, CFSE-labeled PBMCs from healthy individuals were also stimulated with extracellular pathogens for six days. Cell cultures were then re-stimulated with PMA/ionomycin to assess the cytokines profile of proliferating CD4 T cells. Following in vitro expansion, the proportion of subject with detectable antigen-specific (i.e. CFSE$^{low}$) IL-17A-producing CD4 T cells was significantly increased for *C. albicans* and Gram-positive bacteria (P=0.001 and 0.007, respectively) but not for Gram-negative bacteria (FIGS. 1A and B). Furthermore, the frequency of IL-17A-producing cells among the total responding CD4 T cells (i.e. CFSE$^{low}$ cells) also significantly increased after in vitro expansion for *C. albicans* and Gram-positive bacteria (P=0.0001 and 0.004, respectively) but not for Gram-negative bacteria. Interestingly, the proportion of subject with detectable Mtb-specific (CFSE$^{low}$) IL-17A-producing CD4 T cells was significantly (P=0.0002) increased in LTBI but not in TB patients (FIG. 3A-C). In addition, the frequency of Mtb-specific IL-17A-producing CD4 T cells among the total Mtb-specific CD4 T-cell responses (i.e. CFSE$^{low}$) were also significantly increased after in vitro T-cell expansion as compared to direct ex vivo assessment in LTBI subjects (P=0.0027) but not in TB patients (FIGS. 16A, B and D). Of note, the magnitude of Mtb-specific CD4 T-cell proliferation (i.e. CFSE$^{low}$) was not different between LTBI and TB patients (data not shown). Therefore, Mtb-specific Th17 cells were enriched following in vitro T-cell expansion in LTBI subject but not in TB patients, with regards to both the proportion of responders with detectable Th17 cells (P=0.04, FIG. 16C) and the magnitude of IL-17 production (P=0.01, FIG. 16D).

The acquisition of IL-17A effector function by Mtb-specific CD4 T cells in LTBI subjects was found to directly correlate with the proportion of Mtb-specific CD4 T cells co-expressing CCR6 and CXCR3. Th1 and Th17 cells are characterized by the expression of specific chemokine receptors. In this model, Th1 cells express the chemokine receptors CXCR3 (and/or CCR5), while Th17 cells express CCR6, either alone or in combination with CCR4. It was therefore postulated that the capacity of Mtb-specific CD4 T cells from patients with latent Mtb infection to acquire IL-17A effector function might be related to the expression of CXCR3 and/or CCR6. To address this hypothesis, the expression of CXCR3 and CCR6 was assessed by flow cytometry directly ex vivo on Mtb-specific and *C. albicans*-specific (internal control) CD4 T cells on LTBI subjects. In parallel, CFSE-labeled PBMCs from LTBI subjects were stimulated with Mtb-derived antigens or *C. albicans* for six days and then re-stimulated with PMA/ionomycin to assess the cytokines profile of proliferating CD4 T cells as described above. The detection of Mtb-specific or *C. albicans*-specific CD4 T cells was based on the expression of membrane-bound TNF-α (mTNF-α). Of note, the percentage of Mtb-specific CD4 T cells assessed by mTNF-α+ directly correlated with the frequencies of TNF-α-producing Mtb-specific CD4 T cells assessed by intracellular staining (P=0.02, data not shown).

Representative flow cytometric profiles as well as cumulative data show that *C. albicans*-specific CD4 T cells were more represented in the CXCR3−/CCR6+ CD4 T-cell subset (P<0.05) whereas Mtb-specific CD4 T cells were more represented in the CXCR3+/CCR6− CD4 T-cell subset (P<0.05) (FIGS. 17A and B). However, the dominant population of Mtb-specific CD4 T cells was composed of CXCR3+/CCR6+ CD4 T-cell subset (FIGS. 17A and B). Interestingly, the acquisition of IL-17A effector function by Mtb-specific CD4 T cells directly correlated with the proportion of Mtb-specific CD4 T cells co-expressing CXCR3 and CCR6 (P=0.002) (FIG. 17C). Of note, acquisition of IL-17A effector function was not related to the magnitude of antigen-specific CD4 T-cell proliferation (i.e. the percentage CFSE$^{low}$ CD4 T cells), but directly correlated with the level of IL-17A production in the supernatants (P<0.0001; data not shown).

These studies demonstrate the global functional profile of T-cell responses against the Mtb in subjects with latent infection or active disease and for extracellular pathogens in healthy subjects were all significantly different from each other is demonstrated. In contrast to previous studies performed in mice or in humans, the studies described here provide no evidence of an IL-17A immediate effector function (e.g., ex vivo) in the response to Mtb in subjects with latent infection or patients with active TB disease, regardless of the T-cell population assessed (CD4 T cells or CD3+/CD4−/CD8−; data not shown) and the antigens used (ESAT-6, CFP-10 or PPD; data not shown). The potential tissular accumulation of Mtb-specific Th17 cells at the site of pathogen replication (e.g., lung tissue) confirmed the lack of Mtb-specific immediate IL-17A effector function (e.g., ex vivo) in the lung. However, Mtb-specific Th17 cells were detected in about half of LTBI subjects following in vitro expansion but not in TB patients after exposure of mononuclear cells to Mtb antigen. Thus, the control of Mtb infection seems to be associated with the ability to acquire IL-17A effector function.

REFERENCES

Kaufmann, S. H. How can immunology contribute to the control of tuberculosis? *Nat Rev Immunol* 1, 20-30 (2001).

Flynn, J. L. & Chan, J. Immunology of tuberculosis. *Annu Rev Immunol* 19, 93-129 (2001).

Lalvani, A., et al. Enhanced contact tracing and spatial tracking of *Mycobacterium tuberculosis* infection by enumeration of antigen-specific T cells. *Lancet* 357, 2017-2021 (2001).

Ewer, K., et al. Comparison of T-cell-based assay with tuberculin skin test for diagnosis of *Mycobacterium tuberculosis* infection in a school tuberculosis outbreak. *Lancet* 361, 1168-1173 (2003).

Meier, T., Eulenbruch, H. P., Wrighton-Smith, P., Enders, G. & Regnath, T. Sensitivity of a new commercial enzyme-linked immunospot assay (T SPOT-TB) for diagnosis of tuberculosis in clinical practice. *Eur J Clin Microbiol Infect Dis* 24, 529-536 (2005).

Jasmer, R. M., Nahid, P. & Hopewell, P. C. Clinical practice. Latent tuberculosis infection. *N Engl J Med* 347, 1860-1866 (2002).

Betts, M. R., et al. HIV nonprogressors preferentially maintain highly functional HIV-specific CD8+ T cells. *Blood* 107, 4781-4789 (2006).

Harari, A., et al. Functional signatures of protective antiviral T-cell immunity in human virus infections. *Immunol Rev* 211, 236-254 (2006).

Pantaleo, G. & Harari, A. Functional signatures in antiviral T-cell immunity for monitoring virus-associated diseases. *Nat Rev Immunol* 6, 417-423 (2006).

Pantaleo, G. & Koup, R. A. Correlates of immune protection in HIV-1 infection: what we know, what we don't know, what we should know. *Nat Med* 10, 806-810 (2004).

Day, C. L., et al. Detection of polyfunctional *Mycobacterium tuberculosis*-specific T cells and association with viral load in HIV-1-infected persons. *J Infect Dis* 197, 990-999 (2008).

Sutherland, J. S., Adetifa, I. M., Hill, P. C., Adegbola, R. A. & Ota, M. O. Pattern and diversity of cytokine production differentiates between *Mycobacterium tuberculosis* infection and disease. *Eur J Immunol* 39, 723-729 (2009).

Flynn, J. L., et al. Tumor necrosis factor-alpha is required in the protective immune response against *Mycobacterium tuberculosis* in mice. *Immunity* 2, 561-572 (1995).

Feldmann, M. & Maini, R. N. Anti-TNF alpha therapy of rheumatoid arthritis: what have we learned? *Annu Rev Iminunol* 19, 163-196 (2001).

Maini, R., et al. Infliximab (chimeric anti-tumour necrosis factor alpha monoclonal antibody) versus placebo in rheumatoid arthritis patients receiving concomitant methotrexate: a randomised phase III trial. ATTRACT Study Group. *Lancet* 354, 1932-1939 (1999).

Berry, M. P., et al. An interferon-inducible neutrophil-driven blood transcriptional signature in human tuberculosis. *Nature* 466, 973-977.

Lamoreaux, L., Roederer, M. & Koup, R. Intracellular cytokine optimization and standard operating procedure. *Nat Protoc* 1, 1507-1516 (2006).

Harari, A., et al. An HIV-1 Glade C DNA prime, NYVAC boost vaccine regimen induces reliable, polyfunctional, and long-lasting T cell responses. *J Exp Med* 205, 63-77 (2008).

Zimmerli, S. C., et al. HIV-1-specific IFN-gamma/IL-2-secreting CD8 T cells support CD4-independent proliferation of HIV-1-specific CD8 T cells. *Proc Natl Acad Sci USA* 102, 7239-7244 (2005).

Griner, P. F., Mayewski, R. J., Mushlin, A. I. & Greenland, P. Selection and interpretation of diagnostic tests and procedures. Principles and applications. *Ann Intern Med* 94, 557-592 (1981).

Metz, C. E. Basic principles of ROC analysis. *Semin Nucl Med* 8, 283-298 (1978).

Zweig, M. H. & Campbell, G. Receiver-operating characteristic (ROC) plots: a fundamental evaluation tool in clinical medicine. *Clin Chem* 39, 561-577 (1993).

What is claimed is:

1. A method for identifying an individual having active Tuberculosis disease, the method comprising isolating mononuclear cells from the individual, incubating the cells with a peptide derived from *Mycobacterium tuberculosis*, and assaying the CD4 T-cells for expression of TNFα, IFN-γ, and IL-2, wherein the relative percentage of mononuclear CD4 T-cells producing TNFα but not producing IFN-γ or IL-2 is greater than 35%.

2. The method of claim 1 wherein the relative percentage is greater than 37.4%.

3. The method of claim 2 wherein the relative percentage is greater than 38.8%.

4. The method of claim 1 wherein the relative percentage is determined using flow cytometry.

5. A method for monitoring active Tuberculosis disease comprising:
   a) administering to an individual having active Tuberculosis disease with an antibiotic for about 6 months;
   b) isolating mononuclear cells from the individual about 4 weeks, about 3 months and about 6 months after initiation of therapy;
   c) incubating the cells with a peptide derived from *Mycobacterium tuberculosis* and assaying the relative percentage of CD4 T-cells therein producing TNFα, IFN-γ, and IL-2;
   d) determining the relative percentage of mononuclear CD4 T-cells producing TNFα and not producing IFN-γ or IL-2 and, subsequently, either:
      1) continuing administration of the antibiotic therapy where the relative percentage of mononuclear CD4 T-cells producing TNFα and not producing IFN-γ or IL-2 is lower than 35%, or
      2) modifying administration of the antibiotic therapy where the relative percentage of mononuclear CD4 T-cells producing TNFα and not producing IFN-γ or IL-2 remains greater than 35% after about 4 weeks, about 3 months or about 6 months following the initiation of the antibiotic therapy.

6. The method of claim 5 wherein the relative percentage in step d1 is lower than 37.4%.

7. The method of claim 6 wherein the relative percentage in step d1 is lower than 38.8%.

8. The method of claim 5 wherein the relative percentage in step d2 is greater than 37.4%.

9. The method of claim 6 wherein the relative percentage in step d2 is greater than 38.8%.

10. The method of claim 5 wherein the antibiotic therapy comprises administering to the individual drug selected from the group consisting of isoniazid, rifmpicin pyrazinamide, ethambutol, streptomycin, an aminoglycoside, amikacin, kanamycin, a polypeptide, capreomycin, viomycin, enviomycin, a fluoroquinolone, ciprofloxacin, levofloxacin, moxifloxacin, a thioamide, ethionamide, prothionamide, cycloserine, p-aminosalicylic acid, rifabutin, a macrolide, clarithromycin, linezolid, thioacetazone, thioridazine, arginine, vitamin D, R207910, and combinations thereof.

11. The method of claim 5 wherein the antibiotic therapy of step d1 is selected from the group consisting of isoniazid alone, rifampin for four months, daily administration of isoniazid and rifampin for three months, and administration of rifampin and pyrazinamide for two months.

12. The method of claim 5 wherein the antibiotic therapy of step d2 is selected from the group consisting of isoniazid, rifmpicin, pyrazinamide, and ethambutol; and isoniazid and rifampicin alone.

13. The method of claim 5 wherein the relative percentage is determined using flow cytometry.

14. The method of claim 5 further comprising repeating b), c), and d).

15. The method of claim 1 further comprising exposing mononuclear cells of the individual to one or more Mtb antigens and detecting the expression of IL-17.

16. The method of claim 15 wherein the expression of IL-17 in the mononuclear cells exposed to the one or more Mtb antigens indicates the patient has latent Mtb infection.

17. The method of claim 16 wherein the wherein the relative percentage of mononuclear CD4 T-cells producing TNFα but not producing IFN-γ or IL-2 is less than 35%.

* * * * *